(12) United States Patent
Rodriguez et al.

(10) Patent No.: US 10,473,645 B2
(45) Date of Patent: Nov. 12, 2019

(54) METHODS FOR IDENTIFYING A RECEPTOR FOR A LIGAND AND USES THEREOF

(71) Applicant: UNIVERSITE DE GENEVE, Geneva (CH)

(72) Inventors: Ivan Rodriguez, Geneva (CH); Alan Jacques Henri Cyrus Carleton, Denges (CH); Daniel Rossier, Geneva (CH)

(73) Assignee: UNIVERSITE DE GENEVE, Geneva (CH)

( * ) Notice: Subject to any disclaimer, the term of this patent is extended or adjusted under 35 U.S.C. 154(b) by 52 days.

(21) Appl. No.: 15/506,266

(22) PCT Filed: Aug. 25, 2015

(86) PCT No.: PCT/EP2015/069454
§ 371 (c)(1),
(2) Date: Feb. 24, 2017

(87) PCT Pub. No.: WO2016/030378
PCT Pub. Date: Mar. 3, 2016

(65) Prior Publication Data
US 2017/0285009 A1    Oct. 5, 2017

(30) Foreign Application Priority Data

Aug. 26, 2014 (EP) .................................... 14182350

(51) Int. Cl.
| | |
|---|---|
| G01N 33/50 | (2006.01) |
| G01N 33/566 | (2006.01) |
| C12N 5/0793 | (2010.01) |
| G01N 33/68 | (2006.01) |
| A01K 67/027 | (2006.01) |

(52) U.S. Cl.
CPC ..... *G01N 33/5041* (2013.01); *A01K 67/0275* (2013.01); *A01K 67/0278* (2013.01); *C12N 5/0619* (2013.01); *G01N 33/5058* (2013.01); *G01N 33/566* (2013.01); *G01N 33/6872* (2013.01); *A01K 2207/15* (2013.01); *A01K 2217/052* (2013.01); *A01K 2227/105* (2013.01); *A01K 2267/03* (2013.01); *C12N 2510/00* (2013.01); *G01N 2333/705* (2013.01); *G01N 2333/726* (2013.01); *G01N 2500/10* (2013.01)

(58) Field of Classification Search
CPC ............ G01N 33/5041; G01N 33/566; G01N 2333/705; G01N 2500/10; G01N 2333/726; G01N 33/5058; C12N 5/0619; C12N 2510/00
See application file for complete search history.

(56) References Cited

FOREIGN PATENT DOCUMENTS

| EP | 1 391 508 | 2/2004 |
|---|---|---|
| WO | WO 00/35274 | 6/2000 |
| WO | WO 01/68805 | 9/2001 |
| WO | WO 03/020913 | 3/2003 |

OTHER PUBLICATIONS

Araneda, R. C. et al. "The molecular receptive range of an odorant receptor" *Nature Neuroscience*, Dec. 2000, pp. 1248-1255, vol. 3, No. 12.
Bavan, S. et al. "Discovery of Novel Ligands for Mouse Olfactory Receptor MOR42-3 Using an In Silico Screening Approach and In Vitro Validation" *PLOS One*, Mar. 2014, pp. 1-11, vol. 9, Issue 3, e92064.
Bozza, T. et al. "Odorant Receptor Expression Defines Functional Units in the Mouse Olfactory System" *The Journal of Neuroscience*, Apr. 15, 2002, pp. 3033-3043, vol. 22, No. 8.
Hallem, E. A. et al. "Coding of Odors by a Receptor Repertoire" *Cell*, Apr. 7, 2006, pp. 143-160, vol. 125.
Huang, Y.-J. et al. "Mouse Taste Buds Use Serotonin as a Neurotransmitter" *The Journal of Neuroscience*, Jan. 26, 2005, pp. 843-847, vol. 25, No. 4.
Kaupp, U. B. et al. "Olfactory signalling in vertebrates and insects: differences and commonalities" *Nature*, Mar. 2010, pp. 188-200, vol. 11.
Knight, Z. A. et al. "Molecular Profiling of Activated Neurons by Phosphorylated Ribosome Capture" *Cell*, Nov. 21, 2012, pp. 1126-1137, vol. 151.
Malnic, B. et al. "Combinatorial Receptor Codes for Odors" *Cell*, Mar. 5, 1999, pp. 713-723, vol. 96.
Murrell, J. R. et al. "An Olfactory Sensory Neuron Line, Odora, Properly Targets Olfactory Proteins and Responds to Odorants" *The Journal of Neuroscience*, Oct. 1, 1999, pp. 8260-8270, vol. 19, No. 19.
Nagashima, A. et al. "Enzymatic Conversion of Odorants in Nasal Mucus Affects Olfactory Glomerular Activation Patterns and Odor Perception" *The Journal of Neuroscience*, Dec. 1, 2010, pp. 16391-16398, vol. 30, No. 48.
Nishizumi, H. et al. "Decoding and deorphanizing an olfactory map" *Nature Neuroscience*, Oct. 2015, pp. 1432-1433, vol. 18, No. 10.
Oka, Y. et al. "Odorant Receptor Map in the Mouse Olfactory Bulb: In Vivo Sensitivity and Specificity of Receptor-Defined Glomeruli" *Neuron*, Dec. 7, 2006, pp. 857-869, vol. 52.
Peterlin, Z. etal. "The state of the art of odorant receptor deorphanization: A report from the orphanage" *The Journal of General Physiology*, 2014, pp. 527-542, vol. 143, No. 5.

(Continued)

*Primary Examiner* — Ruixiang Li
(74) *Attorney, Agent, or Firm* — Saliwanchik, Lloyd & Eisenschenk

(57) ABSTRACT

The present invention relates to a novel method for identifying pairs of receptors/ligands, transgenic animals useful for carrying out said method, and the use of ligands and/or modulators of the interaction between a ligand and its receptor in the food industry, fragrance industry, and health industry, for instance.

12 Claims, 9 Drawing Sheets

Specification includes a Sequence Listing.

(56) References Cited

OTHER PUBLICATIONS

Richgels, P. K. et al. "Genetic Variation in Odorant Receptors Contributes to Variation in Olfactory Behavior in a Natural Population of *Drosophila melanogaster*" *Chemical Senses*, Oct. 29, 2011, pp. 229-240, vol. 37.

Rinker, D. C. et al. "Novel high-throughput screens of *Anopheles gambiae* odorant receptors reveal candidate behaviour-modifying chemicals for mosquitoes" *Physiological Entomology*, 2012, pp. 33-41, vol. 37.

Rivière, S. et al. "Formyl peptide receptor-like proteins are a novel family of vomeronasal chemosensors" *Nature*, May 28, 2009, pp. 574-577, vol. 459.

Shirokova, E. et al. "Identification of Specific Ligands for Orphan Olfactory Receptors" *The Journal of Biological Chemistry*, Mar. 25, 2005, pp. 11807-11815, supplemental pp. 1-6, vol. 280, No. 12.

Thiebaud, N. et al. "Odorant Metabolism Catalyzed by Olfactory Mucosal Enzymes Influences Peripheral Olfactory Responses in Rats" *PLOS One*, Mar. 2013, pp. 1-13, vol. 8, Issue 3, e59547.

Trimmer, C. et al. "High-throughput Analysis of Mammalian Olfactory Receptors: Measurement of Receptor Activation via Luciferase Activity" *Journal of Visualized Experiments*, Jun. 2014, pp. 1-10, vol. 88, e51640.

Vassalli, A. et al. "Homeodomain binding motifs modulate the probability of odorant receptor gene choice in transgenic mice" *Molecular and Cellular Neuroscience*, Feb. 2011, pp. 381-396, vol. 46, No. 2.

Vassalli, A. et al. "Minigenes Impart Odorant Receptor-Specific Axon Guidance in the Olfactory Bulb" *Neuron*, Aug. 15, 2002, pp. 681-696, vol. 35.

Von der Weid, B. et al. "Large-scale transcriptional profiling of chemosensory neurons identifies receptor-ligand pair in vivo" *Nature Neuroscience*, Oct. 2015, pp. 1455-1465, supplemental pp. 1-2, vol. 18, No. 10.

Zhang, J. et al. "Ultrasensitive Detection of Amines by a Trace Amine-Associated Receptor" *The Journal of Neuroscience*, Feb. 13, 2013, pp. 3228-3239, vol. 33, No. 7.

Written Opinion in International Application No. PCT/EP2015/069454, Feb. 18, 2016, pp. 1-9.

METHODS FOR IDENTIFYING A RECEPTOR FOR A LIGAND AND USES THEREOF

CROSS-REFERENCE TO RELATED APPLICATION

This application is the U.S. national stage application of International Patent Application No. PCT/EP2015/069454, filed Aug. 25, 2015.

The Sequence Listing for this application is labeled "Seq-List.txt" which was created on Jan. 24, 2017 and is 8 KB. The entire content of the sequence listing is incorporated herein by reference in its entirety.

FIELD OF THE INVENTION

The present invention relates to the identification of chemoreceptors responding to defined chemical molecules or blend of chemical molecules, i.e. identifying pairs of receptor/ligand, and the application of the knowledge of such a relationship in any industry including food industry, fragrance industry, and health industry.

BACKGROUND OF THE INVENTION

Animals have evolved various types of chemosensory tools to perceive the outside world. Among these are the taste and the olfactory systems. Specialized chemosensors are expressed in these structures. Depending on the species, these may include for example G protein-coupled receptors (GPCRs) such as odorant receptors (ORs), vomeronasal receptors (VRs), trace amine receptors (TAARs), formyl peptide receptors (FPRs), T1R and T2R taste receptors, and non-GPCRs such as transient receptor potential (Trp) channels, guanylyl cyclases, and olfactory ionotropic receptors (IRs) (Kaupp, 2010, *Nature Rev. Neuroscience*, 11: 188-200). These sensors allow the animals to face the immense variety of external stimuli, in particular via their ORs, which allows them to detect and discriminate billions of different molecules. The gene repertoire encoding these receptors is diverse inside a given species, and is variable between species, both in terms of size and in terms of contents. In the mouse, for example, the OR repertoire reaches 1'250 members, which represents over 5% of its total number of genes. Every olfactory sensory neuron expresses a single olfactory receptor gene, which means that hundreds of functionally different populations of sensory neurons coexist in the nasal cavity. Each of these populations can be activated by various agonists, and each agonist can be recognized by various ORs. This leads to a combinatorial code, which allows discrimination between different blends.

In the last 30 years, in a process called deorphanization, ligands and antagonists have been assigned to a large fraction of GPCRs. This is to the exception of ORs, which remain orphans for their largest part. For example, over 90% of human ORs are still orphans (Peterlin et al., 2014, *J. Gen. Physiol.*, 143, 527-542). Individual OR deorphanization is important, but even more interesting would be to provide a list of ORs that respond to a given chemical in a given species. Today, in mice or humans, not a single odorant molecule is known for which an exhaustive list of cognate ORs has been defined. Such knowledge could be very valuable for understanding the combinatorial code at the base of the sense of smell, but could also have commercial applications. For example, the knowledge of the OR repertoire activated by a given odorant would be helpful for mimicking given olfactory stimuli, particularly those with positive hedonic values in humans (like chocolate or flowers). Alternatively this could allow the discovery of odorant antagonists blocking the perception of undesired odors or flavors (like unpleasant body odors or the smell of sewers). Taken as a whole, it would facilitate our ability to modulate specific chemosensory percepts.

The limited number of deorphanized ORs, to date, does not result from a lack of efforts, but rather from a lack of suitable assays. Most known olfactory agonist-receptor pairs were identified in vitro. These approaches involved the expression of rodent or human chemoreceptors in heterologous systems, including xenopus oocytes, yeasts, ovarian insect cells, baculoviruses, and native or engineered HEK and Hela cells (Peterlin et al., 2014, supra). These expression systems brought significant advances and allowed the deorphanization (that is to find at least one activating molecule) and characterization of 41 human and 95 mouse ORs. However, these non-native methodologies suffer from significant downsides. First, ORs produced in vitro are usually retained in the endoplasmic reticulum and thus fail to reach the cell membrane. Their fusion with segments of non-olfactory proteins is therefore often chosen for heterologous expression, possibly modifying their response profiles. Second, a complex nasal mucus containing odorant binding proteins, that represents the natural interface between receptors and their potential agonists, is absent in vitro. This is critical since this mucus plays an enzymatic role that chemically modifies many odorant molecules (Nagashima and Touhara, 2010, *J. Neurosci.*, 30, 16391-16398). Third, the coupling of the OR to its native transduction cascade, which is usually not recapitulated in vitro, is known to affect receptor-odorant specificities (Shirokova et al., 2005, *J. Biol. Chem.*, 280, 11807-11815). Finally, potential ligands are provided in liquid and not gaseous phase in vitro, making their concentrations difficult to relate to those present during natural ortho- and retronasal fluxes.

To circumvent some of the non-native downsides of heterologous expression, alternative approaches were taken. Efforts to develop in silico models have been made (e.g. Bavan et al., 2014, *PLoS One* 9, e92064). Closer to physiological conditions, responses of olfactory sensory neurons expressing endogenous or exogenous ORs to chemicals were studied (Araneda et al., 2000, *Nat. Neurosci.* 3, 1248-1255; Malnic et al., 1999, *Cell* 96, 713-723; Oka et al., 2006, *Neuron*, 52, 857-869). Other methods based on gene-targeted mice in which defined olfactory sensory neurons were labeled, also proved successful for a handful of ORs. However, these methodologies based on sensory neurons involve ex vivo preparations or complex mouse surgeries, and most importantly, only allow deorphanization of one receptor at a time.

Therefore, there remains a need for a method allowing the rapid and easy identification of the receptors that respond to specific olfactory compounds in vivo, in particular those of special interest like malodor counteracting molecules or smell modulators. Such a method would also constitute a critical tool for large scale screening of agonists and antagonists.

SUMMARY OF THE INVENTION

The inventors found that, unexpectedly, in mice and flies, following in vivo or ex vivo exposure to a chemical stimulus, olfactory sensory neurons which respond to this stimulus quickly modulate (upregulate or downregulate) the amount of transcripts corresponding to the olfactory receptor (s) they express. Based on these findings, the present invention provides a simple, fast and efficient method that allows the identification of receptors responding to specific chemical stimuli, based on alterations of mRNA expression. Although primarily illustrated with olfactory receptors/ligands, the present invention can be extended to other chemoreceptors/ligands pairs, to other species, and to transgenic species expressing specific chemoreceptors.

A first aspect of the invention provides a method of identifying at least one chemoreceptor for at least one ligand comprising the steps of:
 a) providing a biological sample comprising cells expressing at least one chemoreceptor, wherein said biological sample (i) has been exposed to at least one test compound or (ii) was obtained from an animal that has been exposed to at least one test compound;
 b) measuring a signal that is proportional to the level of transcription of at least one gene encoding a chemoreceptor in said biological sample,
 c) comparing the level of signal determined in step b) to the level of signal determined in the same conditions with a negative control where the biological sample or animal has not been exposed to said at least one test compound;
 wherein a difference between the level of signal determined in step b) and the level of signal determined in the same conditions with a negative control indicates that said at least one test compound constitutes a ligand for said at least one chemoreceptor and is able to bind and modulate the activity of said at least one chemoreceptor.

A second aspect of the invention relates to a method of identifying an agent able to modulate the binding of a ligand for its chemoreceptor based on the comparison in the level of transcription of a gene encoding said chemoreceptor in presence and absence of ligand and/or test agent.

A third aspect of the invention resides in transgenic non-human animal expressing at least five exogenous chemoreceptor genes.

A fourth aspect of the invention relates to isolated cells such as sensory cells and/or tissues such as tissues present in the olfactory system, extracted from said transgenic non-human animals.

A fifth and sixth aspects of the invention concerns a method for producing said transgenic non-human animals and the use thereof in the methods according to the invention.

A seventh aspect of the invention relates to a ligand binding to a chemoreceptor as well as agents modulating the binding of a ligand to its chemoreceptor, which can be identified by the methods of the invention, as well as compositions comprising said ligand and/or agents.

An eighth aspect of the invention provides a method for modulating the perception of at least one scent and/or at least one taste in a subject comprising the use of at least one ligand of at least one chemoreceptor involved in the perception of said scent and/or taste and/or at least one agent modulating the binding of a ligand to said chemoreceptor.

Other features and advantages of the invention will be apparent from the following detailed description.

DETAILED DESCRIPTION OF THE INVENTION

Figure 1:
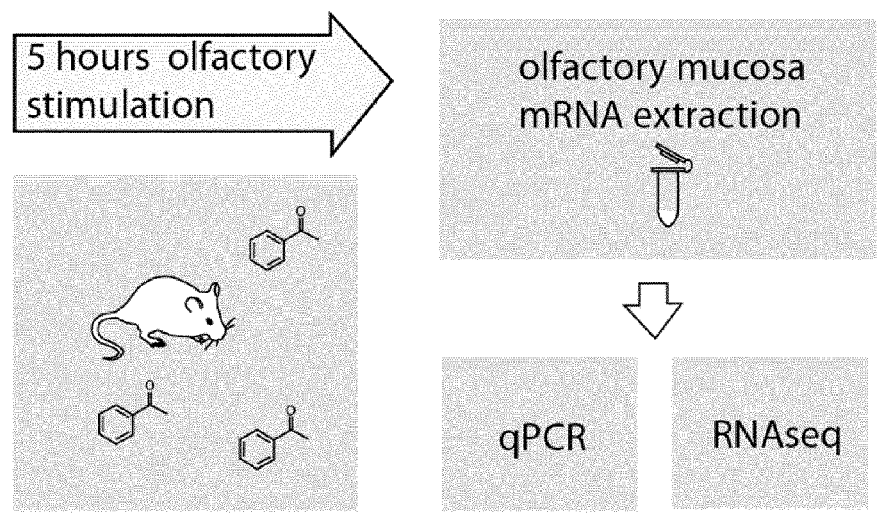
FIG. 1: Olfactory receptor transcript modulation following neuronal activation. (a): Schematic representation of the protocol employed. (b)-(f): Olfactory receptor transcript levels following olfactory stimulation by acetophenone (b), heptanal (c), tetradecanal (d), lyral (e), ethyl isobutyrate (f), and vanillic acid (g). Olfactory receptor gene transcript levels were evaluated by RT-qPCR for each olfactory receptor gene, and the ratios between the values obtained in exposed versus control mice are shown. Olfactory receptors present in the left-side zone correspond to those which were previously shown to respond to the tested volatile. Those present in the right-hand zone were previously shown to be non-responsive to the chemicals. Each dot represents a single mouse. Medians are shown as black horizontal bars, and boxes extend from the $25^{th}$ and the $75^{th}$ percentile. The horizontal grey zone corresponds to values that are not considered as significantly modulated.
Figure 1:
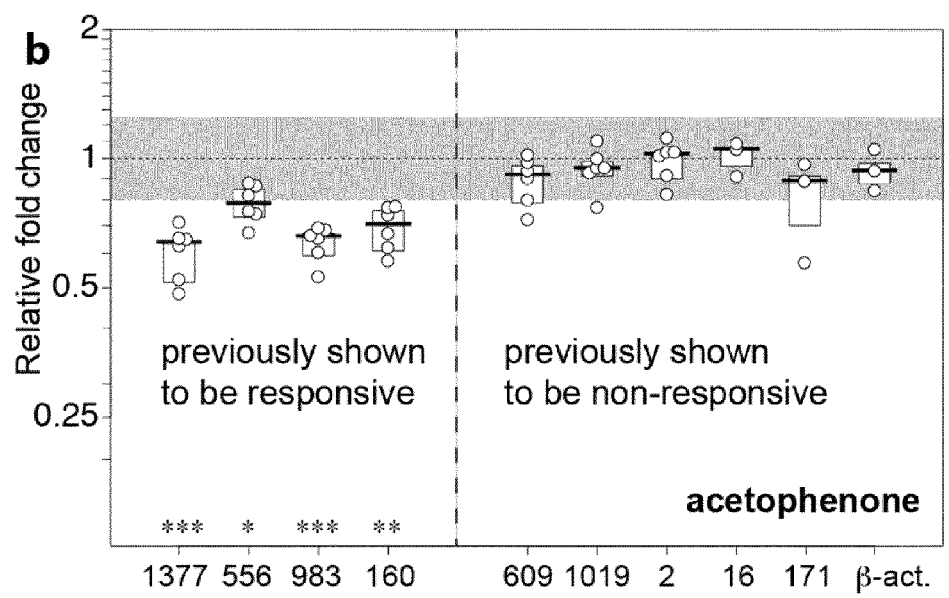
Figure 1:
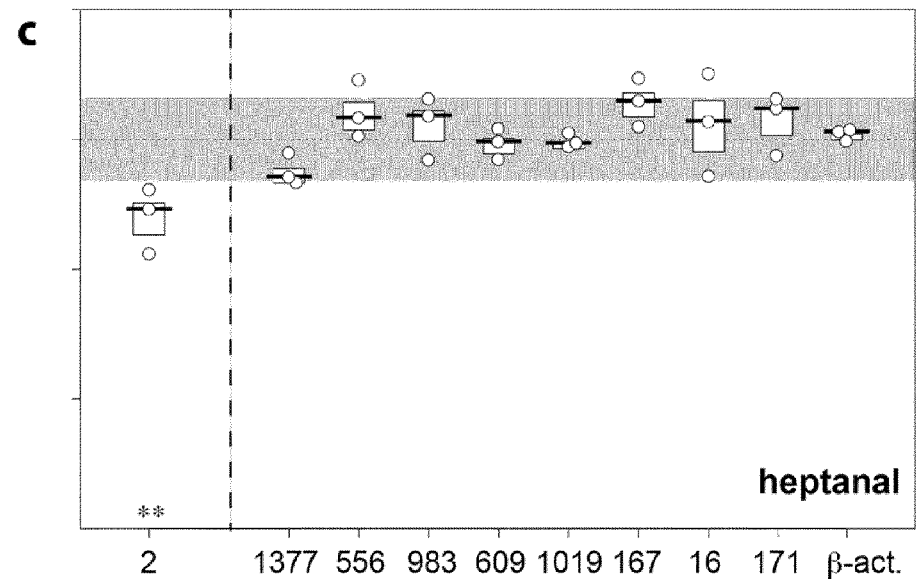
Figure 1:
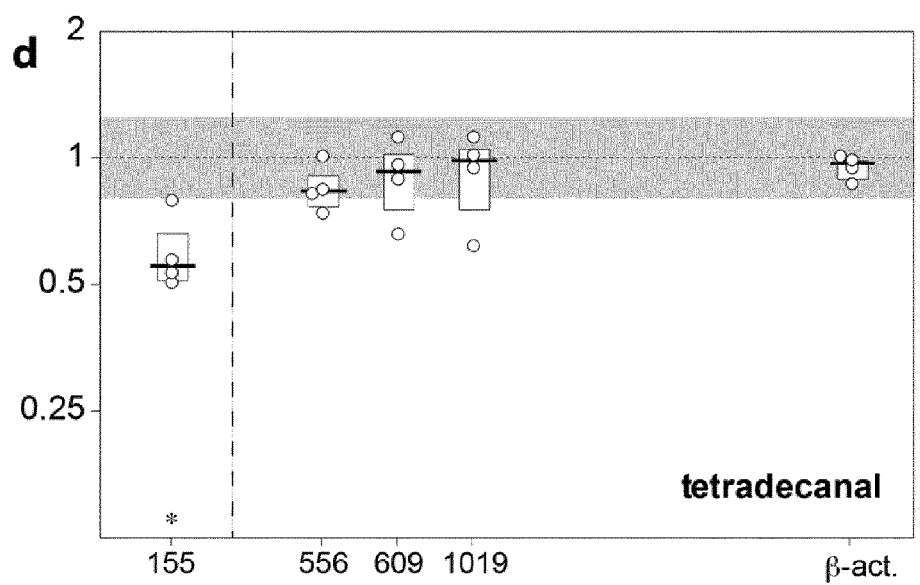
Figure 1:
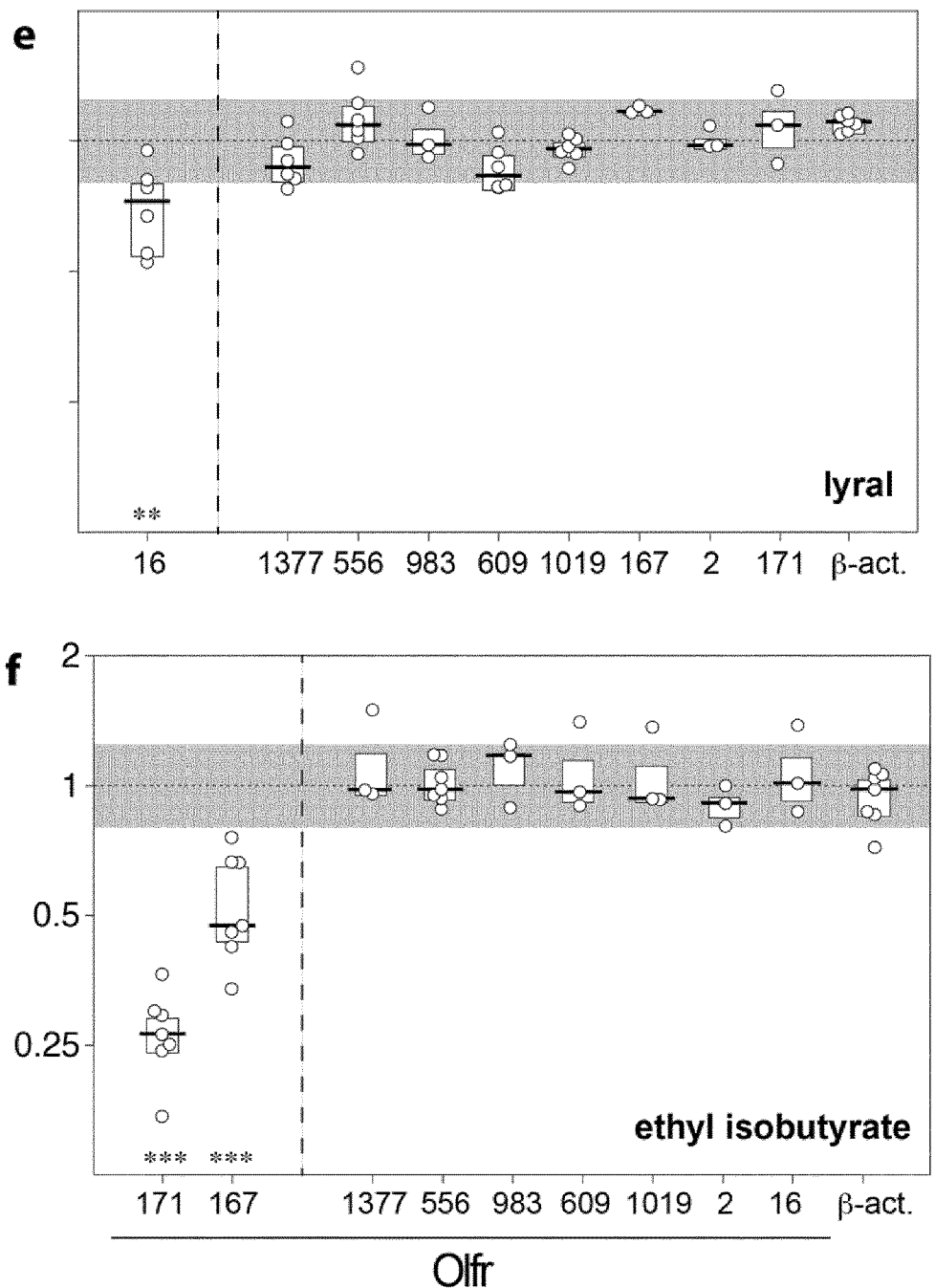
Figure 1:
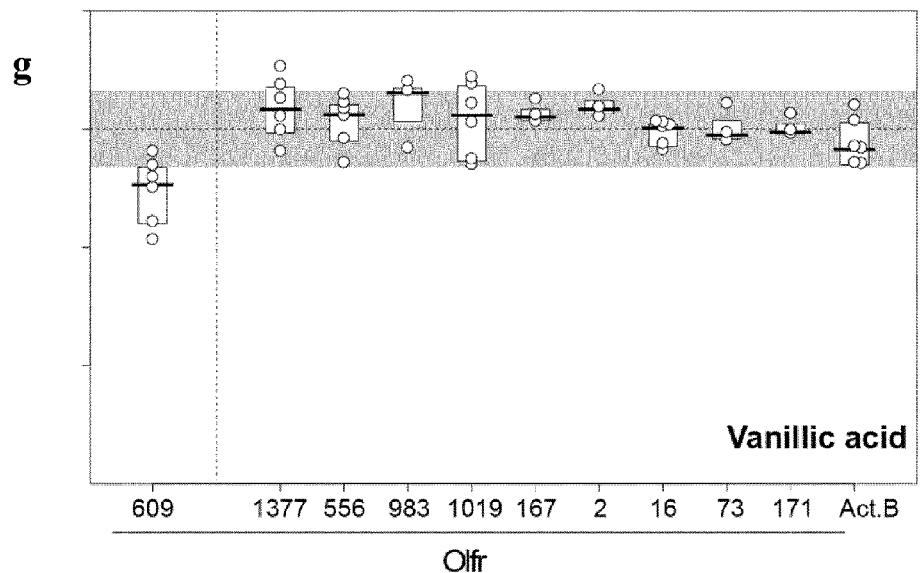

As defined herewith, a "chemoreceptor", also called "chemosensor", is a sensory receptor that transduces a chemical signal into cellular responses. In more general terms, a chemoreceptor detects certain chemical stimuli in the environment. In vertebrates, chemoreceptors include odorant receptors (ORs), trace amine receptors (TAARs), vomeronasal type 1 (V1Rs), vomeronasal type 2 receptors (V2Rs), formyl peptide receptors (FPRs), transient receptor potential (Trp) channels, guanylyl cyclase D and G (GCD/G), taste type 1 receptors (T1Rs), taste type 2 receptors (T2Rs), endothelium non-voltage gated sodium channel (ENaC), polycistic kidney disease 2 like 1 (PKD2L1) channels. In insects, chemoreceptors include ionotropic 7TM ORs, 7TM GRs and ionotropic IRs (Kaupp, 2010, *Nature Rev. Neuroscience*, 11: 188-200).

Chemoreceptors include, for instance, olfactory receptors from the olfactory system, taste (or gustatory) receptors from the gustatory system, Trp channels from the trigeminal system. The term "chemoreceptor" encompasses the polypeptides having the same amino acid sequence as those naturally found in animals, as well as any variant thereof that is biologically active, i.e. that functions as a chemoreceptor.

As used herewith the term "variants" of a chemoreceptor encompasses polypeptides that have a high degree of similarity or a high degree of identity with the amino acid sequence of a chemoreceptor found in nature (e.g. a human chemoreceptor or a murine chemoreceptor) and which are biologically active, i.e. said polypeptides function as chemoreceptors and transduce a chemical signal into cellular responses. In particular, the term "variants" of a chemoreceptor encompasses polypeptides substantially homologous to a reference polypeptide (e.g. defined by a specific amino acid sequence) including orthologous polypeptides found in different species, or an isoform, a mutant, or fragment thereof, e.g. which have an amino acid sequence different from that of the reference polypeptide because of one or more deletions, insertions or substitutions.

Substantially homologous means a variant amino acid sequence that is at least 80%, at least 85%, at least 90%, at least 95%, at least 96%, at least 97%, at least 98% or at least 99% identical to the reference amino acid sequence. The term "variant" also applies to the nucleic acid sequence encoding a chemoreceptor. Applied to a nucleic acid sequence, substantially homologous means a variant nucleic acid sequence that is at least 80%, at least 85%, at least 90%, at least 95%, at least 96%, at least 97%, at least 98% or at least 99% identical to the reference nucleic acid sequence. The "percentage of identity" between two amino acid sequences or between two nucleic acid sequences can be determined by visual inspection and/or mathematical calculation, or more easily by comparing sequence information using known computer programs used for sequence analyses such as Clustal package version 1.83.

As used herewith, "G protein-coupled receptor proteins (GPCRs)", also known as "seven-transmembrane domain receptors", "7TM receptors", "heptahelical receptors", "serpentine receptors", and "G protein-linked receptors (GPLR)", designate a large protein family of receptors that sense molecules outside the cell and activate, inside the cell, signal transductions pathways and, ultimately, cellular responses.

GPCRs are found in eukaryotes, including yeast and animals. The ligands that bind and activate these receptors include light-sensitive compounds, odors, pheromones, hormones, and neurotransmitters, and vary in size from small molecules to peptides to large proteins.

As used herewith, the terms "olfactory receptors" designate the receptors expressed in the cell membranes of olfactory sensory neurons responsible for the detection of chemical cues. Activated olfactory receptors are the initial player in a signal transduction cascade which ultimately produces a nerve impulse which is transmitted to the brain. Most of these receptors are members of the GPCR superfamily. The olfactory receptors form a multigene family consisting of about 400 potentially functional genes in humans and about 1250 genes in mice. Olfactory receptors are generally categorized, in mammals, into several receptor families including odorant receptors (ORs), vomeronasal receptors (V1Rs and V2Rs), trace amine-associated receptors (TAARs), formyl peptide receptors (FPRs), and the membrane guanyl cyclase GC-D.

"Olfactory sensory neurons" (OSNs) designate herewith highly specialized chemo sensory cells found in the nasal compartments constituting the olfactory system including the main olfactory epithelium (MOE), the vomeronasal organ (VNO), the septal organ (SO) and the Grueneberg ganglion (GG). Olfactory sensory neurons allow the perception of odors and pheromones.

As used herewith, the terms "gustatory receptors" include T1Rs, T2Rs, ENaC, PKD2L1 and GRs.

"Gustatory sensory cells" or "taste receptor cells" designate cells expressing gustatory receptors such as T1Rs, T2Rs, ENaC, PKD2L1 or GRs.

The term "ligand" or "chemical stimulus" as used herein refers to a molecule that can bind a chemoreceptor and modulate (activate or inhibit) the function of said chemoreceptor. It follows that a ligand can modulate the downstream signaling activities of its cognate chemoreceptor (e.g., a GPCR) and/or the global olfactory response in the specific case of an olfactory receptor. When a molecule activates a chemoreceptor, it is qualified as "agonist" of said receptor. When a molecule inhibits the activation by an agonist of its cognate chemoreceptor, said molecule is qualified as "antagonist" of said receptor. A ligand for a chemoreceptor can be a molecule of various chemical structures including a peptide, a polypeptide (including an antibody or antigen-binding fragment thereof), a lipid, a carbohydrate, a nucleic acid, a small organic or non-organic molecule including but not limited to an odorant, a fragrance compound and a pheromone, a molecule from a synthetic or natural source, from a chemical or peptide library for instance. A chemical stimulus that can modulate the function of an olfactory receptor is called an "olfactory stimulus".

The term "olfactory stimulus" or "odorant" as used herein comprises any molecule, or group of molecules, volatile or not, aqueous soluble or not, that could interact with an olfactory receptor system such as an olfactory receptor in vivo or an olfactory receptor in vitro expressed in a cell or a tissue. The sources and the identity of pleasant and unpleasant odorants are very diverse. Olfactory stimuli can be molecules such as alkanes, esters, linear terpenes, cyclic terpenes, aromatic, amines, alcohols, aldehydes, ketones, lactones, thiols, gases. Examples of olfactory stimuli include unpleasant body odors such as those found in breath (methanethiol, hydrogen sulfide, dimethyl sulfide, etc.), on the feet (propanoic acid, isovaleric acid, etc.), or on the armpits ((E)-3-methyl-2-hexenoic acid, (S)-3-methyl-3-sulfanyl-hexan-1-ol, 3-hydroxy-3-methylhexanoic acid, propionic acid, androstenone, etc.).

The terms "agonist" and "antagonist" of a chemoreceptor refer herewith to an agent that modulates (activates and inhibits, respectively) the function of said chemoreceptor and, thus, the downstream signaling activities related to said chemoreceptor and/or, in the case of a ligand binding an olfactory receptor for instance, a global olfactory response related to said olfactory receptor. The agonist and antagonist of a chemoreceptor can act by modulating (enhancing and inhibiting, respectively) the binding of a ligand for its chemoreceptor. Said agonist and said antagonist can be of various natures including a peptide, a polypeptide, an antibody or antigen-binding fragment thereof, a lipid, a carbohydrate, a nucleic acid, a small organic or non-organic molecule including but not limited to an odorant, a fragrance compound and a pheromone, a molecule from a synthetic or natural source, from a chemical or peptide library for instance.

The term "transgene" or "exogenous gene" as used herein refers to a foreign gene that is placed into one or more of the cells of an organism (called a "transgenic organism") by introducing said foreign gene by way of human intervention, such as by microinjection, electric shock or by infection with a recombinant virus, into newly fertilized eggs, germ cells or early embryos, for instance. Thus, one or more of the cells of a transgenic animal contains at least one foreign gene (the transgene), which is part of the genetic material of this transgenic animal. It is advantageous that the transgene is contained in the transgenic animal's germ line such that it can be transmitted to the animal's offspring. The term "foreign gene" refers to any nucleic acid (e.g. gene sequence) that is introduced into the genome of an animal by experimental manipulations. The foreign gene generally encompasses the gene sequence of a gene (e.g. of a chemoreceptor such as an olfactory receptor) from a different animal species than the transgenic animal expressing said transgene, e.g. the foreign gene can be a human olfactory receptor gene expressed in a transgenic mouse. A foreign gene may also include a gene sequence found in that animal as long as the introduced gene does not reside in the same location as does the naturally-occurring gene. A foreign gene can also be an "autologous gene" defined as encompassing variants (e.g., polymorphisms or mutants) of the naturally occurring gene.

Methods of Identifying Ligands of Chemoreceptors and/or Agents Modulating the Effect of a Ligand on its Chemoreceptor In a first aspect, the invention provides a method of deorphanizing a chemoreceptor, i.e. identifying at least one ligand of at least one chemoreceptor and, thus, identifying the members of at least one ligand/chemoreceptor pair.

Typically, the binding of a ligand to its chemoreceptor generates the downstream signaling activities related to said chemoreceptor and/or, in the case of a ligand binding an olfactory receptor, a global olfactory response related to said olfactory receptor.

In one embodiment, the invention provides a method of identifying at least one chemoreceptor for at least one ligand comprising the steps of:
  a) providing a biological sample comprising cells expressing at least one chemoreceptor, wherein said biological sample (i) has been exposed to at least one test compound or (ii) was obtained from an animal that has been exposed to at least one test compound;
  b) measuring a signal that is proportional to the level of transcription of at least one gene encoding a chemoreceptor in said biological sample;
  c) comparing the level of signal determined in step b) to the level of signal determined in the same conditions with a negative control where the biological sample or animal has not been exposed to said at least one test compound;
  wherein a difference between the level of signal determined in step b) and the level of signal determined in the same conditions with a negative control indicates that said at least one test compound constitutes a ligand for said at least one chemoreceptor and is able to bind and modulate the activity of said at least one chemoreceptor.

According to one embodiment of the method of the invention, when the level of signal determined in step b) in the biological sample after exposure to at least one test compound is lower than the level of signal determined in the same conditions with a negative control without exposure to a test compound, this indicates that said at least one test compound constitutes a ligand acting as an agonist for said at least one chemoreceptor.

According to another embodiment of the method of the invention, when the level of signal determined in step b) in the biological sample after exposure to at least one test compound is higher than the level of signal determined in the same conditions with a negative control without exposure to a test compound, this indicates that said at least one test compound constitutes a ligand acting as an antagonist for said at least one chemoreceptor.

In the invention, a biological sample typically comprises isolated cells or cells within a tissue, wherein said cells express at least one chemoreceptor and wherein the gene encoding said chemoreceptor was naturally present in said cells or was introduced within said cells by genetic engineering or is present in said cells because said cells have been obtained from a transgenic non-human animal expressing at least one exogenous chemoreceptor gene as described herewith.

According to the invention, said chemoreceptor is selected among a G protein-coupled receptor protein (GPCR) or a non-GPCR protein.

In a particular embodiment of the invention, said chemoreceptor is a GPCR protein, more particularly a receptor selected from the group consisting of an olfactory receptor and a gustatory receptor.

Non-GPCR proteins useful in the invention include Trp channels, GCD/G, ENaC, PCKD channels, ionotropic 7TM ORs, 7TM GRs and ionotropic IRs.

In a particular embodiment, said chemoreceptor is an olfactory receptor.

Examples of human odorant receptors include those listed below, where the reference indicated in brackets provide access to their amino acid sequence and nucleic acid sequence available in public databases:
OR2W1 (ENSG00000229328), OR3A3 (ENSG00000159961), OR5P3 (ENSG00000182334), OR5AN1 (ENSG00000176495), OR11H4 (ENSG00000176198), OR10A3 (ENSG00000170683), OR52I2 (ENSG00000226288), OR7A5 (ENSG00000188269), OR6X1 (ENSG00000221931), OR52I1 (ENSG00000232268), OR4L1 (ENSG00000176246), OR5A2 (ENSG00000172324), OR52B2 (ENSG00000255307), OR4K17 (ENSG00000176230), OR8J1 (ENSG00000262796), OR5P2 (ENSG00000183303), OR56B4

(ENSG00000180919), OR5T3 (ENSG00000261897), OR51D1 (ENSG00000197428), OR6M1 (ENSG00000196099), OR2AG2 (ENSG00000188124), OR8K1 (ENSG00000263328), OR8J1 (ENSG00000172487), OR10K1 (ENSG00000173285), OR4N5 (ENSG00000184394), OR9G4 (ENSG00000262647), OR2H2 (ENSG00000229680), OR4C11 (ENSG00000172188), OR1J4 (ENSG00000239590), OR5T2 (ENSG00000262851), OR4C46 (ENSG00000185926), OR10R2 (ENSG00000198965), OR1N1 (ENSG00000171505), OR5T1 (ENSG00000262784), AC213223.1 (ENSG00000261958), OR1N2 (ENSG00000171501), OR1L8 (ENSG00000171496), OR4M2 (ENSG00000182974), OR5V1 (ENSG00000233046), OR12D2 (ENSG00000235966), OR2W1 (ENSG00000204704), OR4F4 (ENSG00000177693), OR6C75 (ENSG00000187857), OR10W1 (ENSG00000172772), OR2B3 (ENSG00000204703), OR2D3 (ENSG00000178358), OR51L1 (ENSG00000176798), OR8U1 (ENSG00000172199), OR8H2 (ENSG00000181767), OR1K1 (ENSG00000165204), OR7C2 (ENSG00000127529), OR7G3 (ENSG00000170920), OR2AE1 (ENSG00000244623), OR4P4 (ENSG00000181927), OR8K3 (ENSG00000262755), OR4S2 (ENSG00000174982), OR52A5 (ENSG00000171944), OR2Y1 (ENSG00000174339), OR4C6 (ENSG00000181903), OR2V1 (ENSG00000185372), OR8U8 (ENSG00000262315), OR2V2 (ENSG00000182613), OR1D5 (ENSG00000262628), OR2J3 (ENSG00000204701), OR1D2 (ENSG00000184166), OR8K3 (ENSG00000181689), OR4E2 (ENSG00000221977), OR52A1 (ENSG00000182070), OR7D2 (ENSG00000188000), OR13A1 (ENSG00000256574), OR2A42 (ENSG00000212807), OR2A7 (ENSG00000243896), OR4A47 (ENSG00000237388), OR5A1 (ENSG00000172320), OR2J2 (ENSG00000204700), OR8B2 (ENSG00000204293), OR6Y1 (ENSG00000197532), OR6P1 (ENSG00000186440), OR8B3 (ENSG00000196661), OR14J1 (ENSG00000234195), OR10A6 (ENSG00000175393), OR2H1 (ENSG00000204688), OR2W1 (ENSG00000206525), OR8B4 (ENSG00000198657), OR8B8 (ENSG00000197125), OR4D6 (ENSG00000166884), OR8H3 (ENSG00000181761), OR2AG1 (ENSG00000170803), OR56A1 (ENSG00000180934), OR6A2 (ENSG00000184933), OR8J3 (ENSG00000167822), OR8D4 (ENSG00000181518), OR8K5 (ENSG00000181752), OR2A1 (ENSG00000221970), OR1E2 (ENSG00000127780), OR4D5 (ENSG00000171014), OR2F2 (ENSG00000221910), OR2B3 (ENSG00000225736), OR6T1 (ENSG00000181499), OR10S1 (ENSG00000196248), OR10G4 (ENSG00000254737), OR10G9 (ENSG00000236981), OR52J3 (ENSG00000205495), OR10G8 (ENSG00000234560), OR10G7 (ENSG00000182634), OR4K5 (ENSG00000176281), OR10X1 (ENSG00000186400), OR10Z1 (ENSG00000198967), OR5AP2 (ENSG00000172464), OR3A1 (ENSG00000180090), OR3A2 (ENSG00000221882), OR52E2 (ENSG00000155249), OR2B11 (ENSG00000177535), OR4K1 (ENSG00000176787), OR5K2 (ENSG00000231861), OR10C1 (ENSG00000204689), OR5AR1 (ENSG00000172459), OR5R1 (ENSG00000174942), OR10J5 (ENSG00000184155), OR51B6 (ENSG00000176239), OR8B12 (ENSG00000170953), OR8A1 (ENSG00000196119), OR8K1 (ENSG00000150261), OR52D1 (ENSG00000181609), OR1I1 (ENSG00000094661), OR2B3 (ENSG00000206524), OR2C3 (ENSG00000196242), OR14A2 (ENSG00000241128), OR13G1 (ENSG00000197437), OR10A5 (ENSG00000166363), OR6B2 (ENSG00000182083), OR2Z1 (ENSG00000181733), OR9A2 (ENSG00000179468), OR2J3 (ENSG00000206522), OR5M9 (ENSG00000150269), OR6V1 (ENSG00000225781), OR1G1 (ENSG00000183024), OR51B5 (ENSG00000242180), OR9G1 (ENSG00000174914), OR13F1 (ENSG00000186881), OR51Q1 (ENSG00000167360), OR13C4 (ENSG00000148136), OR13C3 (ENSG00000204246), OR6B3 (ENSG00000178586), OR4N4 (ENSG00000183706), OR13C8 (ENSG00000186943), OR51E1 (ENSG00000180785), OR6C65 (ENSG00000205328), OR4F3 (ENSG00000230178), OR7A10 (ENSG00000127515), OR5AC2 (ENSG00000196578), OR5H1 (ENSG00000231192), OR8H1 (ENSG00000262611), OR52N2 (ENSG00000180988), OR52N5 (ENSG00000181009), OR52K2 (ENSG00000181963), OR5B17 (ENSG00000197786), OR5M3 (ENSG00000174937), OR13C5 (ENSG00000277556), OR1F1 (ENSG00000168124), OR52W1 (ENSG00000175485), OR9K2 (ENSG00000170605), OR51M1 (ENSG00000184698), OR52E4 (ENSG00000180974), OR52B6 (ENSG00000187747), OR51B2 (ENSG00000184881), OR52E8 (ENSG00000183269), OR52E6 (ENSG00000205409), OR4F21 (ENSG00000176269), OR52N1 (ENSG00000181001), OR56B1 (ENSG00000181023), OR2F1 (ENSG00000213215), OR12D3 (ENSG00000112462), OR6C76 (ENSG00000185821), OR10C1 (ENSG00000206474), OR12D2 (ENSG00000168787), OR10G2 (ENSG00000255582), OR11H12 (ENSG00000257115), OR5V1 (ENSG00000243729), OR11G2 (ENSG00000196832), OR11A1 (ENSG00000204694), OR1M1 (ENSG00000170929), OR5H14 (ENSG00000236032), OR5J2 (ENSG00000174957), OR1Q1 (ENSG00000165202), OR1B1 (ENSG00000171484), OR7D4 (ENSG00000174667), OR11H1 (ENSG00000130538), OR10V1 (ENSG00000172289), OR52N4 (ENSG00000181074), OR6C70 (ENSG00000184954), OR6C2 (ENSG00000179695), OR1E1 (ENSG00000180016), OR2AP1 (ENSG00000179615), OR6C68 (ENSG00000205327), OR6C4 (ENSG00000179626), OR2J1 (ENSG00000226931), OR51A7 (ENSG00000176895), OR51A4 (ENSG00000205497), OR9G4 (ENSG00000172457), OR51F1 (ENSG00000188069), OR4B1 (ENSG00000175619), OR51G1 (ENSG00000176879), OR51G2 (ENSG00000176893), OR2H2 (ENSG00000204657), OR7A17 (ENSG00000185385), OR10A7 (ENSG00000179919), OR2H2 (ENSG00000206512), OR11H6 (ENSG00000176219), OR6J1 (ENSG00000255804), OR4C13 (ENSG00000258817), OR5AU1 (ENSG00000169327), OR4C12 (ENSG00000221954), OR2J2 (ENSG00000196231), OR51F2 (ENSG00000176925), OR1L1 (ENSG00000173679), OR1L3 (ENSG00000171481), OR51S1

(ENSG00000176922), OR51A2 (ENSG00000205496), OR52R1 (ENSG00000176937), OR8S1 (ENSG00000197376), OR6Q1 (ENSG00000172381), OR9I1 (ENSG00000172377), OR14J1 (ENSG00000237777), OR51H1P (ENSG00000176904), OR14J1 (ENSG00000234100), OR4D10 (ENSG00000254466), OR9Q1 (ENSG00000186509), OR51T1 (ENSG00000176900), OR9A4 (ENSG00000258083), OR4M1 (ENSG00000176299), OR4N2 (ENSG00000176294), OR4Q3 (ENSG00000182652), OR51E2 (ENSG00000167332), OR4A16 (ENSG00000181961), OR51I2 (ENSG00000187918), OR4A15 (ENSG00000181958), OR52H1 (ENSG00000181616), OR5I1 (ENSG00000167359), OR7E24 (ENSG00000237521), OR51V1 (ENSG00000176742), OR13C2 (ENSG00000276119), OR10A2 (ENSG00000170790), OR2J3 (ENSG00000229866), OR6C74 (ENSG00000197706), OR10A4 (ENSG00000170782), OR9Q2 (ENSG00000186513), OR13C9 (ENSG00000136839), OR52K1 (ENSG00000196778), OR4D11 (ENSG00000176200), OR1S2 (ENSG00000197887), OR4D1 (ENSG00000141194), OR5B3 (ENSG00000172769), OR5W2 (ENSG00000187612), OR6B1 (ENSG00000221813), OR5I1 (ENSG00000167825), OR2D2 (ENSG00000166368), OR1S1 (ENSG00000172774), OR4D2 (ENSG00000255713), OR4K15 (ENSG00000169488), OR2K2 (ENSG00000171133), OR2A5 (ENSG00000221836), OR7G2 (ENSG00000170923), OR6K2 (ENSG00000196171), OR2S2 (ENSG00000122718), OR4D9 (ENSG00000172742), OR5D13 (ENSG00000198877), OR5H15 (ENSG00000233412), OR52B4 (ENSG00000221996), OR7G1 (ENSG00000161807), OR10C1 (ENSG00000229412), OR1L4 (ENSG00000136939), OR12D3 (ENSG00000242022), OR10AG1 (ENSG00000174970), OR2A25 (ENSG00000221933), OR5B2 (ENSG00000172365), OR2J1 (ENSG00000204702), OR5K3 (ENSG00000206536), OR6K3 (ENSG00000203757), OR4K14 (ENSG00000169484), OR5H6 (ENSG00000230301), OR10T2 (ENSG00000186306), OR10K2 (ENSG00000180708), OR2AT4 (ENSG00000171561), OR4X2 (ENSG00000172208), OR5K4 (ENSG00000196098), OR5H2 (ENSG00000197938), OR5D14 (ENSG00000186113), OR52M1 (ENSG00000197790), OR12D2 (ENSG00000233481), OR6K6 (ENSG00000180433), OR10J1 (ENSG00000196184), OR4K13 (ENSG00000176253), OR13D1 (ENSG00000179055), OR5D18 (ENSG00000186119), OR4X1 (ENSG00000176567), OR4S1 (ENSG00000176555), OR4C3 (ENSG00000176547), OR4C5 (ENSG00000176540), OR6C6 (ENSG00000188324), OR1J1 (ENSG00000136834), OR4K2 (ENSG00000165762), OR1A2 (ENSG00000172150), OR4F29 (ENSG00000278566), OR2B2 (ENSG00000168131), OR6C1 (ENSG00000205330), OR2AI2 (ENSG00000221858), OR2A4 (ENSG00000180658), OR6C3 (ENSG00000205329), OR5F1 (ENSG00000149133), OR1L6 (ENSG00000171459), OR5AS1 (ENSG00000181785), OR5L2 (ENSG00000205030), OR5D16 (ENSG00000205029), OR5C1 (ENSG00000148215), OR56A3 (ENSG00000184478), OR1A1 (ENSG00000172146), OR13H1 (ENSG00000171054), OR2J2 (ENSG00000231676), OR52L1 (ENSG00000183313), OR4F17 (ENSG00000176695), OR2A2 (ENSG00000221989), OR5B12 (ENSG00000172362), OR6S1 (ENSG00000181803), OR56A4 (ENSG00000183389), OR5T2 (ENSG00000181718), OR5T3 (ENSG00000172489), OR5M11 (ENSG00000255223), OR10AD1 (ENSG00000172640), OR4F16 (ENSG00000273547), OR6F1 (ENSG00000169214), OR10D3 (ENSG00000197309), OR5T1 (ENSG00000181698), OR5M10 (ENSG00000254834), OR1C1 (ENSG00000221888), OR14A16 (ENSG00000196772), OR11L1 (ENSG00000197591), OR8H1 (ENSG00000181693), OR2C1 (ENSG00000168158), OR8I2 (ENSG00000172154), OR2W3 (ENSG00000238243), OR2T8 (ENSG00000177462), OR2AJ1 (ENSG00000177275), OR4F15 (ENSG00000182854), OR4F6 (ENSG00000184140), OR8D1 (ENSG00000196341), OR8D2 (ENSG00000197263), OR2L3 (ENSG00000198128), OR10P1 (ENSG00000175398), OR2L13 (ENSG00000196071), OR2L5 (ENSG00000197454), OR2AK2 (ENSG00000187080), OR2L8 (ENSG00000196936), OR1J2 (ENSG00000197233), OR2L2 (ENSG00000203663), OR2M5 (ENSG00000162727), OR2M2 (ENSG00000198601), OR2M3 (ENSG00000228198), OR2M4 (ENSG00000171180), OR2T33 (ENSG00000177212), OR10G3 (ENSG00000169208), OR5M1 (ENSG00000255012), OR2A14 (ENSG00000221938), OR5B21 (ENSG00000198283), OR2T12 (ENSG00000177201), OR4F5 (ENSG00000186092), OR2M7 (ENSG00000177186), OR14C36 (ENSG00000177174), OR6N2 (ENSG00000188340), OR5K1 (ENSG00000232382), OR2T4 (ENSG00000196944), OR2T6 (ENSG00000198104), OR2T1 (ENSG00000175143), OR2T7 (ENSG00000227152), OR2T2 (ENSG00000196240), OR2B6 (ENSG00000124657), OR7C1 (ENSG00000127530), OR2T3 (ENSG00000196539), OR2T5 (ENSG00000203661), OR2G6 (ENSG00000188558), OR2T29 (ENSG00000182783), OR2T34 (ENSG00000183310), OR2T10 (ENSG00000184022), OR2T35 (ENSG00000177151), OR2T27 (ENSG00000187701), OR14I1 (ENSG00000189181), OR4C15 (ENSG00000181939), OR4C16 (ENSG00000181935).

The sequences of the above-mentioned ORs can be retrieved from the uniprot.org or the ensembl.org (GRCh38 (GCA_000001405.15) assembly) websites.

In a particular embodiment, said olfactory receptor is a human odorant receptor, in particular a human odorant receptor selected from the group consisting of:

OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14A16, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2, OR14I1, OR2C3, OR4A15,

OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR8I2, OR10H1, OR1D2, OR2G6, OR4C13, OR51D1, OR5AK2, OR6C3, OR8J1, OR10OH2, OR1D5, OR2H1, OR4C15, OR51E1, OR5AN1, OR6C4, OR8J3, OR10H3, OR1E1, OR2H2, OR4C16, OR51E2, OR5AP2, OR6C6, OR8K1, OR10H4, OR1E2, OR2J1, OR4C3, OR51F1, OR5AR1, OR6C65, OR8K3, OR10H5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I1, OR2K2, OR4C6, OR51G2, OR5B12, OR6C74, OR8U1, OR10J5, OR1J1, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, OR5C1, OR6K2, OR9G4, OR10R2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, OR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11, OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H4, OR2A12, OR2T27, OR4F6, OR52E2, OR5J2, OR6Y1, OR11H6, OR2A14, OR2T29, OR4K1, OR52E4, OR5K1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2, OR5M11, OR7G1.

In another particular embodiment, said olfactory receptor is a variant of a human odorant receptor, in particular a variant of any one of the human odorant receptors listed above, more particularly a variant having an amino acid sequence having at least 80% identity, for instance at least 85%, at least 90%, at least 95%, at least 96%, at least 97%, at least 98%, or at least 99% identity with the amino acid sequence of a human odorant receptor, in particular with any one of the human odorant receptors listed above.

In one embodiment, said GPCR is a non-OR GPCR.

In a particular embodiment, said chemoreceptor is a human non-OR chemoreceptor, in particular a human non-OR chemoreceptor selected from the group consisting of: a gustatory receptor, a Tip channel, a V1r or a V2r.

In another embodiment, said chemoreceptor is an invertebrate non-GPCR, in particular an insect chemosensor selected from the group consisting of ionotropic 7TM ORs, 7TM GRs and ionotropic IRs.

In a particular embodiment of the method of the invention, said biological sample and the gene encoding said chemoreceptor are from the same species, e.g. a biological sample from a mouse comprises cells expressing a gene encoding a mouse chemoreceptor.

In another particular embodiment, the identification of a mouse chemoreceptor as a receptor for a given ligand can be extended to the receptor or receptors of another species, in particular a human, because of the high sequence homology between the mouse receptor and the human receptor(s). Table 1 provides examples of human odorant receptors and murine odorant receptors which show at least 90% identity in their amino acid sequences.

TABLE 1

| Mouse | Human | Percentage of Identity |
|---|---|---|
| Olfr727 (ENSMUSG00000059488) | OR4K15 (ENSG00000169488) | 93.83 |
| Olfr558 (ENSMUSG00000070423) | OR51E1 (ENSG00000180785) | 93.67 |
| Olfr713 (ENSMUSG00000073898) | OR10A5 (ENSG00000166363) | 93.38 |
| Olfr78 (ENSMUSG00000043366) | OR51E2 (ENSG00000167332) | 93.10 |
| Olfr1019 (ENSMUSG00000075208) | OR5AR1 (ENSG00000172459) | 93.06 |
| Olfr577 (ENSMUSG00000043354) | OR51G2 (ENSG00000176893) | 93.01 |
| Olfr449 (ENSMUSG00000049168) | OR6B1 (ENSG00000221813) | 92.60 |
| Olfr1032 (ENSMUSG00000042796) | OR5M3 (ENSG00000174937) | 92.48 |
| Olfr713 (ENSMUSG00000073898) | OR10A2 (ENSG00000170790) | 92.38 |
| Olfr734 (ENSMUSG00000045306) | OR4M1 (ENSG00000176299) | 91.37 |
| Olfr984 (ENSMUSG00000045812) | OR4D5 (ENSG00000171014) | 90.45 |
| Olfr152 (ENSMUSG00000068816) | OR5I1 (ENSG00000167825) | 90.42 |
| Olfr1510 (ENSMUSG00000063106) | OR10G2 (ENSG00000255582) | 90.32 |
| Olfr981 (ENSMUSG00000046678) | OR10G6 (ENSG00000198674) | 90.28 |
| Olfr554 (ENSMUSG00000073971) | OR52M1 (ENSG00000197790) | 90.22 |
| Olfr1420 (ENSMUSG00000060878) | OR10V1 (ENSG00000172289) | 90.18 |
| Olfr2 (ENSMUSG00000070417) | OR6A2 (ENSG00000184933) | 90.18 |
| Olfr1191-ps1 (ENSMUSG00000081948) | OR4S2 (ENSG00000174982) | 90.03 |
| Olfr1034 (ENSMUSG00000102091) | OR5M9 (ENSG00000150269) | 90.00 |

In another embodiment, said biological sample and the gene encoding said chemoreceptor are from different species, e.g. a biological sample from a rodent comprises cells expressing a gene encoding a human chemoreceptor.

In one embodiment, the biological sample comprises a tissue comprising cells expressing at least one chemoreceptor as described above.

A tissue suitable for the invention typically comprises sensory neurons such as olfactory sensory neurons, gustatory sensory cells, or neurons from the trigeminal system.

Alternatively, a tissue suitable for the invention can comprise sensory cells from the sensillae from the antennae or from the palps in insects.

A tissue suitable for the invention can be selected from the group consisting of: main olfactory epithelium, vomeronasal organ, septal organ, Grueneberg ganglion, trigeminal tissue, sensory tissue from the oral cavity, for example.

In a particular embodiment, said tissue is the main olfactory epithelium.

In another particular embodiment, said tissue is the taste epithelium from the tongue.

In another particular embodiment, said tissue is the sensillae from the antennae or from the palps from an insect.

Said tissues can be obtained from biopsies of animals (including humans, non-human animals or transgenic non-human animals as described herewith), according to methods known in the art.

In another embodiment, the biological sample used in the invention comprises isolated cells expressing at least one chemoreceptor as described above.

The cells suitable for the invention are typically isolated from one of the above described tissues.

The cells suitable for the invention can also be cells from a cell line such as an olfactory sensory neuron cell line like Odora (Murrel and Hunter, 1999, *J. Neurosci.*, 19(19): 8260-70).

In a particular embodiment, the cells suitable for the invention are sensory neurons, in particular olfactory sensory neurons isolated from the olfactory system comprising the main olfactory epithelium, vomeronasal organ, septal organ and/or Grueneberg ganglion of an animal or gustatory sensory cells isolated from the taste epithelium of an animal.

In another embodiment, said olfactory sensory neurons are isolated from the main olfactory epithelium.

In a further embodiment, said olfactory sensory neurons are isolated from the vomeronasal organ epithelium.

In a further embodiment, said olfactory sensory neurons are isolated from the Grueneberg ganglion.

In another embodiment, said gustatory sensory cells are isolated from the taste epithelium of the tongue of an animal.

In an alternative particular embodiment, the cells suitable for the invention are sensory cells isolated from the sensillae from the antennae or from the palps of an insect.

In a still further embodiment, said sensory neurons are isolated from a tissue from a transgenic non-human animal as described herewith.

In a particular embodiment, each cell suitable for the invention expresses one chemoreceptor gene as described herewith.

Methods to extract said olfactory sensory neurons are known in the art and include the method described by (Bozza et al., 2002, *J. Neuro*, 22(8):3033-3043; Rivière et al, *Nature* 2009 May 28; 459(7246):574-7).

Methods to extract said gustatory sensory cells or neurons are known in the art and include the method described in Huang et al., 2005, *J. Neuro.*, 25(4) 843-847.

The tissue or cells suitable for the invention can be obtained from an animal that can be a vertebrate or an invertebrate.

In one embodiment, the animal is a vertebrate such as a mammal.

In a particular embodiment, the animal is a mammal such as a human, a rodent, a pig or a cow.

In a particular embodiment, said animal is a non-human animal.

In a further particular embodiment, said animal is a rodent including mice, rats and rabbits.

In another embodiment, the animal is an invertebrate such as a tick, a fly or a mosquito.

In a still other particular embodiment, said non-human animal is a transgenic animal as described herewith.

In a particular embodiment, said non-human animal is a transgenic animal expressing at least 1, at least 2, at least 5, or at least 10, odorant receptor (OR) gene(s).

More particularly, said non-human animal is a transgenic animal expressing at least one, at least 2, at least 5, or at least 10, heterologous OR genes such as a human OR gene.

In a further particular embodiment, said non-human animal is a transgenic animal expressing at least one, at least 2, at least 5, or at least 10, gene(s) encoding a non-OR chemoreceptor.

More particularly, said non-human animal is a transgenic animal expressing at least one, at least 2, at least 5, or at least 10, heterologous non-OR chemoreceptor gene such as a human non-OR chemoreceptor gene.

According to the invention, the test compound to which the biological sample or the animal has been exposed can be of various natures including a peptide, a polypeptide, a lipid, a carbohydrate, and a small organic or non-organic molecule including but not limited to an odorant, a fragrance compound, a palatable or non-palatable compound, a pheromone, a molecule from a synthetic or natural source, from a chemical or peptide library for instance.

In a particular embodiment, where the sensory neurons express at least one olfactory receptor, the test compound is selected from the group consisting of esters, linear terpenes, cyclic terpenes, aromatic, amines, alcohols, aldehydes, ketones, lactones, thiols, sulfated compounds, alkanes, gases.

In a particular embodiment, where the sensory neurons express at least one gustatory receptor, the test compound is selected from the group consisting of a sugar, an acid, or a fatty compound.

In another embodiment, more than one test compound can be tested in a mixture of several test compounds.

In a particular embodiment, the invention uses the following mixtures of test compounds:
  to mimick the odor of bad breath: volatile sulfur compounds including hydrogen sulfide, methanethiol (methyl mercaptan), dimethylsulfide;
  to mimick the odor of "coffee breath": 3-mercapto-methylbutylformate;
  to mimick the odor of garlic breath: allyl methyl sulfide;
  to mimick the odor caused by flatulence: sulfur containing compounds like hydrogen sulfide, methanethiol, dimethyl sulfide;
  to mimick the underarm odor: 3-methyl-2-hexenoic acid, 3-hydroxy-3-methylhexanoic acid, 3-methyl-3-sulfanylhexan-1-ol:
  to mimick the foot odor: methanethiol, propanoic acid, isovaleric acid. The method of the invention is preceded by the exposure of the cells comprised in the biological sample to at least one test compound.

Said exposure can be carried out ex vivo, i.e. cells or tissues expressing at least one chemoreceptor are exposed to said test compound, or in vivo, i.e. the cells or tissues expressing at least one chemoreceptor are from an animal that has been exposed to said test compound.

In general, the method of the invention is preceded by the exposure of the biological sample or animal to the test compound, which lasted for about a few hours such as about 5 hours.

In one embodiment of the methods of the invention, the level of transcription of at least one gene encoding a chemoreceptor is determined. In particular, the level of transcription of at least 5, at least 10, at least 50, or at least 100 genes encoding a chemoreceptor is determined.

In another embodiment of the methods of the invention, the level of transcription of between about 10 and 2000 genes, for instance between about 20 and about 300, between about 20 and about 200 genes, encoding a chemoreceptor is determined.

The level of transcription of a gene can be determined according to standard methods in the field for quantifying said gene's transcript, including methods based on reverse transcription polymerase chain reaction (RT-PCR), mRNA sequencing. Examples of methods to determine the level of transcription of ORs include quantitative RT-PCR (herewith abbreviated "RT-qPCR") and high-throughput mRNA sequencing as illustrated in the example section.

In a second aspect, the invention provides a method of identifying an agent able to modulate the action of a ligand on its chemoreceptor, comprising the steps of:
- (a) Providing 3 sub-samples derived from the same biological sample comprising cells expressing at least one chemoreceptor;
- where said sub-samples have been treated as follows:
  - (i) a first sub-sample has been exposed to a ligand of said chemoreceptor,
  - (ii) a second sub-sample has been exposed to the same ligand of said chemoreceptor as in (i) and to a test agent,
  - (iii) a third sub-sample has not been exposed to either a ligand of said chemoreceptor nor to a test agent, and constitutes a negative control,
- (b) Measuring a signal that is proportional to the level of transcription of the gene encoding said chemoreceptor in each of said three sub-samples;
- (c) Comparing the level of signal determined for each of said three sub-samples, wherein:
  - (i) a level of signal determined in said second sub-sample that is lower than the level of signal determined in said first sub-sample, and a level of signal determined in said first sub-sample that is lower than the level of signal determined in said third sub-sample, indicates that said agent enhances binding of said ligand to said chemoreceptor, and is an agonist of said chemoreceptor,
  - (ii) a level of signal determined in second sub-sample that is equal or comparable to the level of signal determined in said third sub-sample, and a level of signal determined in said second sub-sample and/or said third sub-sample that is higher than the level of signal determined in said first sub-sample, indicates that said agent inhibits the binding of said ligand to said chemoreceptor, and is an antagonist of said chemoreceptor, and
  - (iii) a level of signal determined in said first sub-sample that is equal or comparable to the level of signal determined in said second sub-sample, and a level of signal determined in said first sub-sample and/or said second sub-sample that is lower than the level of signal determined in said third sub-sample, indicates that said agent does not modulate the binding of said ligand to said chemoreceptor.

In a particular embodiment, said method of identifying an agent able to modulate the binding of a ligand to its chemoreceptor further comprises the steps of exposing said biological sample to a ligand for said chemoreceptor alone and in combination with a test agent.

In a more particular embodiment, it is provided a method of identifying an agent able to modulate the binding of a ligand for its chemoreceptor, comprising the steps of:

- (a) Providing a biological sample comprising cells expressing at least one chemoreceptor,
- (b) Dividing said biological sample into 3 groups,
- (c) (i) Exposing a first group of said biological sample to a ligand of said chemoreceptor,
  - (ii) Measuring a signal that is proportional to the level of transcription of the gene encoding said chemoreceptor in said first group,
- (d) (i) Exposing a second group of said biological sample to the same ligand of said chemoreceptor as in (c) (i) and to a test agent,
  - (ii) Measuring a signal that is proportional to the level of transcription of the gene encoding said chemoreceptor in said second group,
- (e) (i) Keeping a third group of said biological sample as negative control with no exposition to either a ligand of said chemoreceptor nor to a test agent,
  - (ii) Measuring a signal that is proportional to the level of transcription of the gene encoding said chemoreceptor in said third group,
- (f) Comparing the level of signal determined in steps (c), (d), and (e),
- wherein:
  - (i) a level of signal determined in step (d) that is lower than the level of signal determined in step (c), and a level of signal determined in step (c) that is lower than the level of signal determined in step (e), indicates that said agent enhances binding of said ligand to said chemoreceptor, and is an agonist of said chemoreceptor,
  - (ii) a level of signal determined in step (d) that is equal or comparable to the level of signal determined in step (e), and a level of signal determined in step (d) and/or (e) that is higher than the level of signal determined in step (c), indicates that said agent inhibits the binding of said ligand to said chemoreceptor, and is an antagonist of said chemoreceptor, and
  - (iii) a level of signal determined in step (c) that is equal or comparable to the level of signal determined in step (d), and a level of signal determined in step (c) and/or (d) that is lower than the level of signal determined in step (e), indicates that said agent does not modulate the binding of said ligand to said chemoreceptor.

The same particular embodiments regarding the chemoreceptor, the biological sample, the tissue, the cells, the determination of the level of transcription of the gene encoding a chemoreceptor, as detailed above for the first aspect of the invention also apply to the method of the invention of this second aspect.

In a particular embodiment of the method of identifying an agent able to modulate the binding of a ligand for its chemoreceptor according to the invention, said biological sample comprises sensory neurons or a tissue comprising sensory neurons, in particular olfactory sensory neurons or a tissue comprising olfactory neurons.

In another particular embodiment of said method, said chemoreceptor is an olfactory receptor, more particularly a human olfactory receptor.

In a further particular embodiment of said method, said biological sample comprises olfactory sensory neurons or a tissue comprising olfactory sensory neurons, wherein said neurons express at least one, at least 5, or at least 10 human olfactory receptor genes.

In a particular embodiment, the duration of exposure to the test agent and/or ligand is of about few hours such as about 5 hours.

The agent to be tested in the methods of the invention can be of various natures including a peptide, a polypeptide, an antibody or antigen-binding fragment thereof, a lipid, a carbohydrate, a nucleic acid, a small organic or non-organic molecule including but not limited to an odorant, a fragrance compound and a pheromone, a molecule from a synthetic or natural source, from a chemical or peptide library for instance.

Transgenic Animals and Use thereof

The invention also provides transgenic non-human animals expressing at least one exogenous chemoreceptor gene such as a human chemoreceptor gene, e.g. a human odorant receptor gene or a human non-odorant receptor gene, or a chemoreceptor gene not normally expressed in said non-human animals.

As will be understood by the skilled person, specifying that a transgenic animal expresses at least one exogenous chemoreceptor gene implies that the genome of said animal, or at least some cells of said animal, comprises said at least one exogenous chemoreceptor gene or its coding sequence.

In a particular aspect, the transgenic non-human animals according to the invention are vertebrates or invertebrates.

In a more particular aspect, the transgenic non-human animals according to the invention are vertebrates including mammals.

In a more particular aspect, the transgenic non-human animal according to the invention is a mammal such as a rodent, a pig or a cow.

In a more particular aspect, the transgenic non-human animal according to the invention is a rodent such as a mouse or a rat.

In a more particular embodiment, the transgenic non-human animal according to the invention is a mouse.

In another particular aspect, the transgenic non-human animals according to the invention are invertebrates, in particular insects, including flies and mosquitoes.

In a particular embodiment, the transgenic non-human animal according to the invention expresses at least one, in particular at least 2, at least 5, at least 10, at least 50, at least 100, for instance from 10 to 2000, more particularly from about 20 to about 300 or from about 20 to about 200, exogenous chemoreceptor genes.

In a more particular embodiment, the transgenic non-human animal according to the invention expresses at least 5 or at least 10 exogenous chemoreceptor genes.

In a particular embodiment, the transgenic non-human animal according to the invention expresses at least one, in particular at least 2, at least 5, at least 10, at least 50, at least 100, for instance from 10 to 384, human odorant receptor gene(s) selected from the group consisting of: OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14A16, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2, OR14I1, OR2C3, OR4A15, OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR8I2, OR10H1, OR1D2, OR2G6, OR4C13, OR51D1, OR5AK2, OR6C3, OR8J1, OR10H2, OR1D5, OR2H1, OR4C15, OR51E1, OR5AN1, OR6C4, OR8J3, OR10H3, OR1E1, OR2H2, OR4C16, OR51E2, OR5AP2, OR6C6, OR8K1, OR10H4, OR1E2, OR2J1, OR4C3, OR51F1, OR5AR1, OR6C65, OR8K3, OR10H5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I1, OR2K2, OR4C6, OR51G2, OR5B12, OR6C74, OR8U1, OR10J5, OR1J1, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, OR5C1, OR6K2, OR9G4, OR1OR2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, OR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11, OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H4, OR2A12, OR2T27, OR4F6, OR52E2, OR5J2, OR6Y1, OR11H6, OR2A14, OR2T29, OR4K1, OR52E4, ORSK1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2, OR5M11, OR7G1; and/or any variant thereof having at least 80% identity, for instance at least 85%, at least 90%, at least 95%, at least 96%, at least 97%, at least 98%, or at least 99% identity with any one of said human odorant receptor gene's sequences.

In a further particular embodiment, the transgenic non-human animal according to the invention expresses at least one, at least 2, at least 5, at least 10, at least 50, at least 100, for instance from 10 to 209, human odorant receptor gene(s) selected from the group consisting of: OR1I1, OR10H5, OR8H1, OR13G1, OR8G5, OR2S2, OR10AD1, OR5T1, OR6Y1, OR52B2, OR7C1, OR4D9, OR8H2, OR11L1, OR4D2, OR11H1, OR5B3, OR52A1, OR8G1, OR13C5, OR1J1, OR10W1, OR6B2, OR2T6, OR13A1, OR13C9, OR10K1, OR5P3, OR2L3, OR13C2, OR1L4, OR1L1, OR2V2, OR5B21, OR11H12, OR4D1, OR2Y1, OR4Q3, OR2M2, OR9A4, OR13C4, OR7D4, OR2T29, OR10Z1, OR11H2, OR5C1, OR5M3, OR4F15, OR2T5, OR5M9, OR10A6, OR4M2, OR2L2, OR4K1, OR52W1, OR2T11, OR6K3, OR1Q1, OR11H4, OR51B4, OR13C3, OR1K1, OR11H6, OR5P2, OR8B2, OR4K2, OR4K17, OR52L1, OR2H2, OR10A5, OR4K13, OR56A4, OR11A1, OR2D2, OR4F21, OR2T10, OR14J1, OR51E2, OR5AN1, OR1D2, OR2J2, OR51I1, OR4F17, OR4N5, OR2J3, OR51Q1, OR51L1, OR56A3, OR6C1, OR8J3, OR51G2, OR51M1, OR52E6, OR2C1, OR2T33, OR51B2, OR5K3, OR12D2, OR2AJ1, OR6A2, OR2F1, OR13J1, OR2T8, OR6C70, OR6B1, OR10G3, OR2B11, OR4F16, OR2A5, OR6F1, OR4F4, OR2V1, OR3A2, OR5AU1, OR2D3, OR7A17, OR1C1, OR4K14, OR6B3, OR4F5, OR2F2, OR9K2, OR13D1, OR9Q1, OR2A25, OR10A3, OR9A2, OR9Q2, OR2A14, OR10A4, OR6C4, OR10H1, OR4E2, OR2AG1, OR6C2, OR2AK2, OR52B4, OR1M1, OR3A1, OR2T27, OR6V1, OR8B12, OR10Q1, OR52B6, OR52I2, OR2K2, OR10K2, OR51I2, OR2M3, OR2M4, OR51E1, OR7D2, OR4F3, OR1L6, OR56B4, OR2AG2, OR5K2, OR1L3, OR56A1, OR7A5, OR52I1, OR1B1, OR52E4, OR2G6, OR5K1, OR1N2, OR52N2, OR2L13, OR5H15, OR1N1, OR52N1, OR2C3, OR4F29, OR2AT4, OR52N5, OR10S1, OR5H14, OR52A5, OR56B1, OR8D1, OR7E24, OR5A1, OR52N4, OR8B3, OR2W3, OR5A2, OR5AK2, OR14A16, OR1J4, OR5B12, OR6T1, OR52K1, OR5V1, OR5B2, OR8D4, OR2L8, OR2AE1, OR9I1, OR52D1, OR8B8, OR4D10, OR6Q1, OR52H1, OR1J2, OR10G4, OR9G4, OR8K3, OR6N1, OR5M10; and/or any variant thereof having at least 80% identity, for instance at least 85%, at least 90%, at least 95%, at least 96%, at least 97%, at least 98%, or at least 99% identity with any one of said human odorant receptor gene's sequences.

The above list of 209 genes corresponds to a group of ORs expressed in most humans.

In a further embodiment, said transgenic non-human animal according to the invention expresses at least one human non-OR chemoreceptor gene, such as at least one, at least 2, at least 5, at least 10, human TAAR receptor genes. More particularly, said transgenic non-human animal according to the invention expresses at least 5 human non-OR chemoreceptor genes.

In a still further embodiment, the transgenic animal according to the invention is a mouse expressing at least one, at least 5, at least 10, at least 50, at least 100, for instance from 10 to 209, human odorant receptor gene(s) selected from the group described above. In a more particular embodiment, said transgenic animal according to the invention is a mouse expressing at least 5 human odorant receptor gene(s) selected from the group described above.

The transgenic non-human animal expressing at least one exogenous chemoreceptor gene according to the invention can be generated by standard procedures in the field including integration of said at least one chemoreceptor gene in said animal's genome following injection of at least one nucleic acid comprising said at least one chemoreceptor gene into oocyte pronuclei or delivery to the oocyte or germ cell by electroporation, viral vector, lipofection, or transfection.

A number of techniques may be used to introduce the transgene into an animal's genetic material, including, but not limited to, microinjection of the transgene into pronuclei of fertilized eggs and manipulation of embryonic stem cells (e.g. Palmiter and Brinster, 1986, *Ann. Rev. Genet*, 20: 465-499). Transgenic animals can carry the transgene in all their cells or can be genetically mosaic.

According to the method of conventional transgenesis, additional copies of normal or modified genes are injected into one of the pronuclei of the zygote and become integrated into the genomic DNA of the recipient animal. The transgene is transmitted in a Mendelian manner in established transgenic strains. Transgenes can be constitutively expressed or can be tissue specific or even responsive to an exogenous drug. A transgenic animal expressing one transgene or multiple transgenes can be crossed to a second transgenic animal expressing a second transgene or multiple transgenes such that their offspring will carry and express all transgenes.

According to one aspect, a transgenic animal of the invention is used as a tool to identify chemoreceptors responding to specific ligands according to a method of the invention.

Thus, in a further aspect, the invention provides a method for making a transgenic animal expressing at least one exogenous chemoreceptor comprising introducing into the genome of said animal a nucleic acid comprising at least one exogenous chemoreceptor gene or its coding sequence.

In a particular embodiment, said nucleic acids comprising said at least one exogenous chemoreceptor gene are bacterial artificial chromosomes (BACs) of typically 80-300 kb comprising said at least one chemoreceptor gene.

In a more particular embodiment, said nucleic acids comprising said at least one human odorant receptor gene are bacterial artificial chromosomes (BACs) of typically 80-300 kb comprising said at least one human odorant receptor gene.

In an alternative embodiment, said nucleic acids comprising said at least one exogenous chemoreceptor gene are short transgenes comprising said chemoreceptor gene's promoter followed by a 5'UTR, an intron, said chemoreceptor gene's coding sequence, and a polyA signal.

In a particular embodiment, said nucleic acids comprising said at least one human odorant receptor gene are short transgenes comprising an human odorant receptor gene's promoter followed by a 5'UTR, an intron, a human odorant receptor gene's coding sequence, and a polyA signal.

In a particular embodiment, the transgenic non-human animal expressing at least one, at least 5, at least 10, at least 50, at least 100, at least 200, human odorant receptor gene(s) according to the invention is generated by the integration, into said animal's genome, of at least one, at least 5, at least 10, at least 50, at least 90, bacterial artificial chromosomes selected from the group consisting of:
CTD-2184G2, RP11-160E10, RP11-378I20, RP11-635I20, RP11-81H21, RP11-100O19, RP11-163E6, RP11-379F1, RP11-652F7, RP11-826F2, RP11-100F1, RP11-177D5, RP11-382A12, RP11-656I18, RP11-846G12, RP11-1029E16, RP11-203G14, RP11-384C21, RP11-659M23, RP11-910P5, RP11-1040N14, RP11-206D24, RP11-409C1, RP11-65A10, RP11-918H8, RP11-1042J13, RP11-21N2, RP11-429J13, RP11-661M13, RP11-947H5, RP11-1044H15, RP11-236L12, RP11-42G15, RP11-663K1, RP11-950A2, RP11-105B16, RP11-23F9, RP11-430I15, RP11-681D10, RP11-95I18, RP11-1069J21, RP11-242C5, RP11-432E18, RP11-696P18, RP11-960L8, RP11-1105A4, RP11-243N6, RP11-438H8, RP11-69E17, RP11-98N22, RP11-1107C18, RP11-24N17, RP11-452G22, RP11-69N15, RP11-98P19, RP11-110A12, RP11-25I15, RP11-454O22, RP11-720H19, RP4-669L17, RP11-1115M8, RP11-259N2, RP11-456D1, RP11-74B15, RP11-1144E12, RP11-27N2, RP11-462C5, RP11-759P17, RP11-1150B23, RP11-297D12, RP11-466F22, RP11-75J4, RP11-115H4, RP11-299I2, RP11-585F1, RP11-76K18, RP11-1205H24, RP11-30H21, RP11-599O3, RP11-777K22, RP11-126P23, RP11-320A14, RP11-62C23, RP11-79N3, RP11-144C16, RP11-

345A24, RP11-630D14, RP11-806H4, RP11-146C10, RP11-361I19, RP11-632E19, RP11-806P5.

The sequence of the above-mentioned BACs can be retrieved from public databases at (see Worldwide Website: ncbi.nlm.nih.gov/clone/).

In a further particular embodiment, the transgenic non-human animal according to the invention that expresses the 209 human odorant receptor genes listed above is generated by the integration, into said animal's genome, of the 94 bacterial artificial chromosomes listed above.

A further aspect of the invention provides a cell isolated from said transgenic non-human animal, in particular a sensory neuron (such as an olfactory sensory neuron isolated from said transgenic non-human animal), as well as a tissue sample extracted from said transgenic non-human animal, in particular a tissue sample extracted from the olfactory system of said transgenic animal.

Said cells and tissues can be isolated as described in the previous sections.

Another aspect of the invention provides the use of the transgenic non-human animal as described herewith, or a cell or a tissue thereof, in the method of identifying at least one chemoreceptor for at least one ligand according to the invention and/or in the method of identifying an agent able to modulate the binding of a ligand for its chemoreceptor according to the invention.

Compositions Useful in the Invention

In another aspect, the invention provides a ligand binding to a chemoreceptor, in particular an olfactory receptor, as well as agents modulating the binding of a ligand to its chemoreceptor, which can be identified by the methods of the invention.

Ligands of at least one chemoreceptor and agents modulating the binding of a ligand to its chemoreceptor, as those identified by the methods according to the invention, are useful for controlling perceived scents and/or tastes. For instance, undesired scents can be blocked, covered or altered by using antagonists of an olfactory receptor and desired scents can be enhanced by using a ligand and/or an agonist of an olfactory receptor.

Ligands of at least one olfactory receptor and agents modulating the binding of a ligand to its olfactory receptor, as those identified by the methods according to the invention, are useful in methods of treatment and/or prevention of disorders involving a chemoreceptor.

Thus, the invention provides compositions comprising at least one ligand of at least one chemoreceptor and/or at least one agent modulating the binding of a ligand to its chemoreceptor.

In a particular embodiment, the invention provides a composition mimicking or reducing the perception of a scent and/or of a taste in a subject, comprising (a) at least one ligand for at least one first chemoreceptor and/or at least one agent modulating the binding of a ligand to a first chemoreceptor.

Uses of Ligands and Agents According to the Invention

The invention provides a method for modulating the perception of at least one scent and/or at least one taste in a subject comprising the use of at least one ligand of at least one chemoreceptor involved in the perception of said scent and/or taste and/or at least one agent modulating the binding of a ligand to said chemoreceptor.

In a particular embodiment, the invention provides a method for modulating the perception of at least one scent in a subject comprising the use of at least one ligand of at least one olfactory receptor involved in the perception of said scent and/or at least one agent modulating the binding of a ligand to said olfactory receptor.

In a more particular embodiment, the invention provides a method for enhancing the perception of at least one scent in a subject comprising the use of at least one ligand of at least one olfactory receptor involved in the perception of said scent and/or at least one agonist of said olfactory receptor.

In another particular embodiment, the invention provides a method for reducing the perception of at least one scent in a subject comprising the use of at least one antagonist of at least one olfactory receptor involved in the perception of said scent.

In the method for modulating the perception of at least one scent and/or at least one taste in a subject according to the invention, various means for exposing said subject to said ligand and/or antagonist can be used including pulverization of said components in the form of an aerosol or incorporating said components in a solid or liquid form in the food or beverage of said subject.

As used herewith, a subject encompasses any animal including a human, a rodent, a cow, a pig, or an insect.

In a particular embodiment, said ligand and/or said agonist and/or antagonist have been identified with the methods of the invention described herewith.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

Animals

Male C57BL/6 mice were ordered at 7 weeks of age from Charles River Laboratories (www.criver.com). Upon arrival they were stored in double filter-equipped disposable plastic cages (Innovive) in groups of 5-6 for 5 days. They were kept in an overpressurized "experimental odorant-free" room. After 5 days mice were isolated into identical cages until they were needed for an experiment (from 1 to 7 days).

*Drosophila* (W1118) were collected between 0 and 14 hours after hatching. Males and females were exposed separately. Gender did not affect their responses, and the data for both sexes were thus pooled.

Odorant Exposures

In vivo exposure to odorant: Starting 48 h before experiments, mice were habituated to pure DMSO on a cotton ball. 200 µl were pipetted directly onto the cotton and placed in the cage, replacing any cotton that was already in the cage for nest-making purposes.

The DMSO cotton ball was then changed daily until the experiment began.

On the day of the experiment, mice receiving odorants were transferred to a different room, where they were exposed to a cotton ball on which 200 µl of odorant diluted in pure DMSO were deposited. Exposures started in the morning between 8 and 10 am (that is two hours after lights were on) and mice were killed and dissected between 1 and 3 pm. Mice did not react differently to cotton balls containing odorants or only DMSO. If a number of different odorants were tested in the same experiment, a different overpressurized room would always be used for each odorant to avoid odor cross-contamination.

Figure 2:
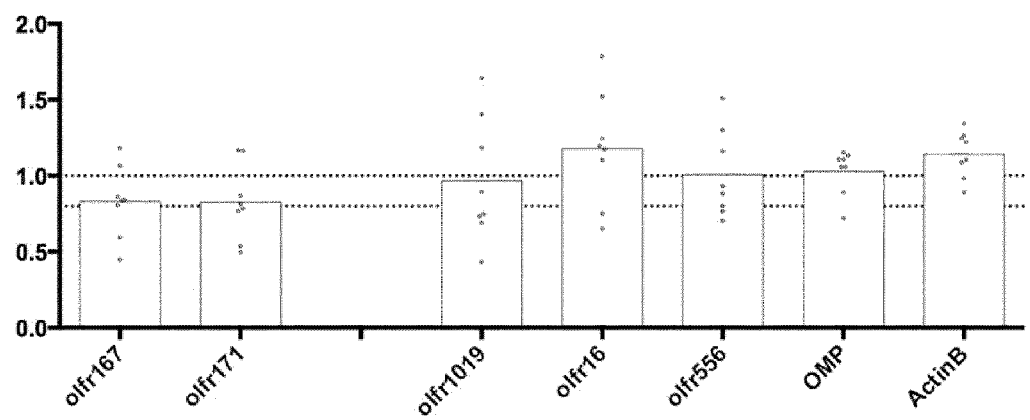
FIG. 2: Olfactory receptor transcript modulation after in vitro ethylisobutyrate exposure. Olfactory receptor gene transcript levels were evaluated by RT-qPCR for each olfactory receptor gene, and the ratios between the values obtained in exposed versus control mice are shown. Olfactory receptors present in the left-side zone correspond to those which were previously shown to respond to the tested volatile. Those present in the right-hand zone were previously shown to be non-responsive to the chemicals.

In vitro exposure to odorant: The olfactory sensory mucosa of a live or recently dead vertebrate is collected and maintained alive in vitro. Sensory neurons are either left untouched or are dissociated. The exposure to the odorants is then performed in vitro, in a tube, in the liquid phase. The explants/neurons are kept alive in a physiological medium (such as 145 mM NaCl, 5 mM KCl, 1 mM $CaCl_2$, 1 mM $MgCl_2$, 10 mM HEPES, 10 mM glucose). The procedure is then comparable to the one used for in vivo exposure, that is to divide the collected sensory neurons in two separate populations, and activate one of these populations (for 2-5 hours but this can be variable) while the other one is used as a negative control. The potential modulations of mRNA levels between the two populations are then evaluated, by qPCR (FIG. 2), RNAseq or other techniques, to identify the receptors that have been activated.

RNA Extractions

After odorant exposure, mice were killed by cervical dislocation and immediately decapitated. The main olfactory epithelia (MOE), were harvested in their entirety and transferred to a tube containing 600 µl of lysis buffer and β-mercaptoethanol (RNAeasy kit, Qiagen, following the manufacturer protocol) and a 0.5 cm diameter steel ball, and then put on ice. Samples were then homogenized using a FastPrep®-24 instrument (MP Biomedicals) at 6 m/s for 30 s and left on ice. RNA extraction was performed on all samples in parallel using the Qiagen RNeasy Mini® kit following the manufacturer's instructions. Two DNase treatments were performed on all samples: first using the Qiagen RNase-Free DNase Set® and then using the Life Technologies Ambion DNase I® kit. RNA samples were then aliquoted and stored at −80° C.

For flies, after exposure, vials containing the animals were placed upside down in a −80° C. freezer for five minutes, then kept in a −20° C. freezer until dissection. Whole heads were removed by hand and placed in a screw-cap tube containing 1 ml of Trizol (Ambion) and a 0.5 cm diameter steel ball, and kept on ice. Samples were homogenized using four runs of 15 s at 6 m/s on a FastPrep®-24 instrument (MP Biomedicals).

Samples were cooled on ice between each run. RNA extraction followed the Trizol protocol according to the manufacturer instructions, and using 5 µg of RNase-free glycogen as carrier for RNA precipitation. The RNA pellet was resuspended in 20 µl of RNase-free water and a DNAse treatment (Life Technologies Ambion DNase I®) was performed.

qPCR

RNA concentrations were determined using an Amersham Ultrospec® 3100 Pro spectrophotometer, and RNA quality was evaluated with an Agilent Technologies 2100 Bioanalyzer®. Each reverse transcription was performed with 0.5 µg RNA using the Takara Primescript® kit, in a final volume of 10 µl. Primers for reverse transcription were equal mixtures of poly-T nucleotides and random hexamers. Negative controls (omitting the reverse transcriptase enzyme) were performed for each sample. 1/14th of the cDNA preparation was used for each triplicated qPCR reaction. The forward and reverse primers for carrying out the qPCR reactions were as presented in Table 2 below.

TABLE 2

| Gene name | ENSMUST Accession Number | SEQ ID NO. forward primer | SEQ ID NO. reverse primer |
|---|---|---|---|
| Olfr160 | 00000104875 | 1 | 2 |
| Olfr556 | 00000098219 | 3 | 4 |
| Olfr1377 | 00000075177 | 5 | 6 |
| Olfr983 | 00000050996 | 7 | 8 |
| Olfr1079 | 00000111582 | 9 | 10 |
| Olfr609 | 00000055787 | 11 | 12 |
| Olfr611 | 00000078108 | 13 | 14 |
| Olfr2 | 00000094109 | 15 | 16 |
| Olfr168 | 00000078554 | 17 | 18 |
| Olfr167 | 00000054606 | 19 | 20 |
| Olfr109 | 00000031086 | 21 | 22 |
| Olfr15 | 00000080917 | 23 | 24 |
| Olfr16 | 00000038432 | 25 | 26 |
| Olfr73 | 00000099838 | 27 | 28 |
| Olfr171 | 00000079891 | 29 | 30 |
| Olfr1019 | 00000102634 | 31 | 32 |
| Omp | 00000098281 | 33 | 34 |
| Adcy3 | 00000020984 | 35 | 36 |
| b Actin | 00000100497 | 37 | 38 |

RT-qPCR was performed on a 7900HT SDS® thermocycler from Applied Biosystems.

Every reaction was systematically run in triplicate. Conditions were the following: 50° C. 2 min, 95° C. 10 min, 40× (95° C. 15 sec, 60° C. 1 min), using SYBR Green® dye.

Raw data were analyzed using the SDS® 2.2.1 software. Detection threshold was set at $\Delta Rn=0.3$, with this limit always within the 2n exponential amplification phase of genes. Dissociation curves were checked for aspecific products and samples were discarded if such products were detected.

qPCR Ct values were analyzed using an in-house developed Microsoft Excel® macro file. Triplicate values were compared and outliers (values with a difference higher than 0.5 Ct to their nearest neighbor) were discarded. The number of conditions with an outlying value was always less than 10% of the total number of conditions. Ct values were converted to quantities relative to the maximum for each given gene. Selected reference genes were then analyzed for variance using the geNorm algorithm. All values were normalized with the olfactory tissue-specific genes Omp and Adcy3. β-Actin was used as a non-tissue-specific reference gene to control for differences in dissection between samples.

RNAseq

Animals were exposed to 5% acetophenone for 5 hours before RNA extraction (as previously described). cDNA libraries were generated with the Truseq RNA and DNA sample preparation kits after selection of polyA-containing mRNAs. Adapters for RNAseq multiplexing were added to the cDNAs. The cDNA libraries were sequenced with a HiSeq®2500 Sequencing system. 100 bp reads were mapped using Bowtie2 with a 28 bp seed. The differential gene expression analyses were performed with DESeq2. Because of the high sequence similarity between OR gene paralogs, some reads are mapped to multiple OR genes. These reads were removed from the analysis.

Example 1

Method of the Invention For Deorphanizing Odorant Receptors in Mice, With In Vivo Exposure to Odorant Adult C57BL/6 mice were exposed to 5% ethyl isobutyrate for 5 hours, and the level of transcripts of odorant receptors' genes were measured by RT-qPCR on extracts of olfactory epithelia from these mice, as described in the materials and methods section.

In the sensory neuroepithelium of adult C57BL/6 mice, the mRNA concentration of Olfr171 and Olfr167, was significantly decreased when exposed to 5% ethyl isobutyrate for 5 hours (ethylisobutyrate was previously shown to be an agonist for Olfr 171 and Olfr67) (74% and 47% relative to unexposed controls respectively, n=7 mice) (FIG. 1a, f). The concentration of none of the control odorant receptor genes (8 genes) was significantly affected by ethyl isobutyrate exposure (a margin of ±20% relative to control mice was considered not significant for the in vivo exposure approach, grey zone on FIG. 1).

To test if this activation-induced transcript downregulation was specific to ethyl isobutyrate-responsive olfactory sensory neurons, or was a general characteristic shared by activated olfactory neurons, the transcriptional responses of 7 additional odorant receptor genes were evaluated.

The products of these genes were previously shown to have as agonists (with an EC50 of less than 50 µM), acetophenone (to which Olfr1377, Olfr556, and Olfr983 are responsive when expressed in HEK cells, and to which Olfr160 is responsive in dissociated neurons), heptanal (to which Olfr2 responds in HEK cells), lyral (to which Olfr16 responds in dissociated neurons), and vanillic acid (to which Olfr609 is responsive in HEK cells). Mice (n=21) were individually exposed for 5 hours to 5% of each of the 4 compounds. The concentration of their corresponding receptor mRNAs was evaluated by RT-qPCR immediately after exposure. For the 7 receptor-ligand pairs, a decrease in mRNA levels relative to unexposed controls was observed (FIG. 1b-e).

In none of the control receptor genes (whose products were previously shown in vitro not to respond to the specific ligands) did we observe such decrease of odorant receptor transcript levels (6-9 genes per condition, FIG. 1).

The potential response to agonist exposure of TAAR genes, that encode the second class of olfactory receptor present in the mammalian olfactory mucosa, was then tested using the same method as the one used for ORs, except that ligand exposure lasted 48 hours.

Figure 6:
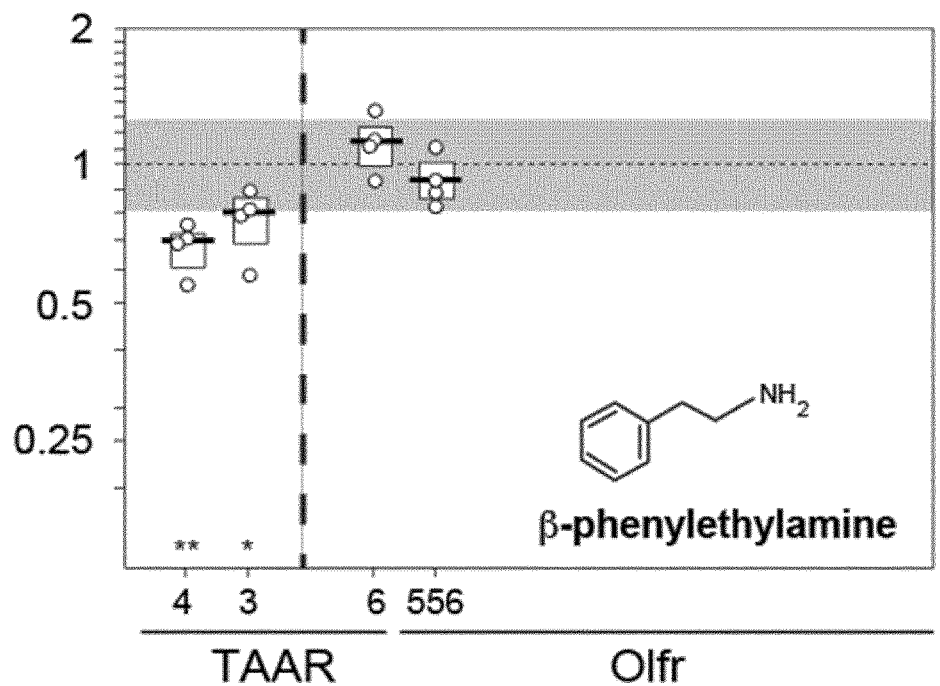
FIG. 6: TAAR transcript modulation following neuronal activation. Transcript levels of olfactory receptor genes were evaluated in mice following olfactory stimulation during 48 hours by beta-phenylethylamine as described in Example 7. Olfactory receptor gene transcript levels were evaluated by RT-qPCR for each receptor gene, and the ratios between the values obtained in exposed versus control mice are shown. "TAAR" correspond to the olfactory receptor genes (trace amine receptor gene) previously shown to respond to beta-phenylethylamine and "olfr" correspond to the olfactory receptor genes which were previously shown to be non-responsive to the chemicals. Each dot represents a single mouse. Medians are shown as black horizontal bars, and boxes extend from the 25$^{th}$ and the 75$^{th}$ percentile. The horizontal grey zone corresponds to values that are not considered as significantly modulated.

Transcript levels of olfactory receptor gene were evaluated following olfactory stimulation during 48 hours by beta-phenylethylamine. Olfactory receptor gene transcript levels were evaluated by RT-qPCR for each receptor gene, and the ratios between the values obtained in exposed versus control mice are shown in FIG. 6. A decrease in the number of transcripts encoding TAAR3 and TAAR4 was observed (two TAAR genes previously shown to respond to this ligand) (Zhang et al, *J. Neurosc.* 2013, 33(7), 3228-3239). The negative controls TAAR6 and Olfr556 were not affected by beta-phenylethylamine (FIG. 6).

These results establish a remarkable correlation between in vitro-identified receptor/ligand pairs, and a specific in vivo transcriptional effect each of these ligands had on neurons expressing the corresponding receptor gene. Therefore, this demonstrates that a transcript-based receptor deorphanization approach can be used to identify, in vivo, novel receptor/ligand pairs and that the present technique applies to a very large variety of chemoreceptors across receptor types.

Example 2

Method of the Invention For Deorphanizing Odorant Receptors in Mice, With Ex Vivo Exposure to Odorant Mouse olfactory epithelia were collected and kept in vitro in ACSF medium where they were exposed for 2 hours to 50 µM ethyl isobutyrate. The number of transcripts for Olfr genes was then evaluated by qPCR, and those of Olfr167 and Olfr171 were both repressed after agonist exposure. Ethyl isobutyrate was previously shown to be an agonist for Olfr167 and Olfr171.

Example 3

Large Scale Odorant Receptor Deorphanization According to the Method of the Invention Examples 1 and 2 demonstrate a solid correlation between olfactory neuron activation and olfactory receptor mRNA downregulation. Current example aimed at demonstrating the feasibility of the method of the invention as a large scale method for receptor deorphanization following olfactory stimulation. An RNAseq approach was chosen to evaluate potential modulations of olfactory receptor gene transcripts.

Acetophenone was tested, which downregulates the messenger levels of Olfr1377, Olfr556, Olfr983 and Olfr160 (FIG. 1).

Figure 3:
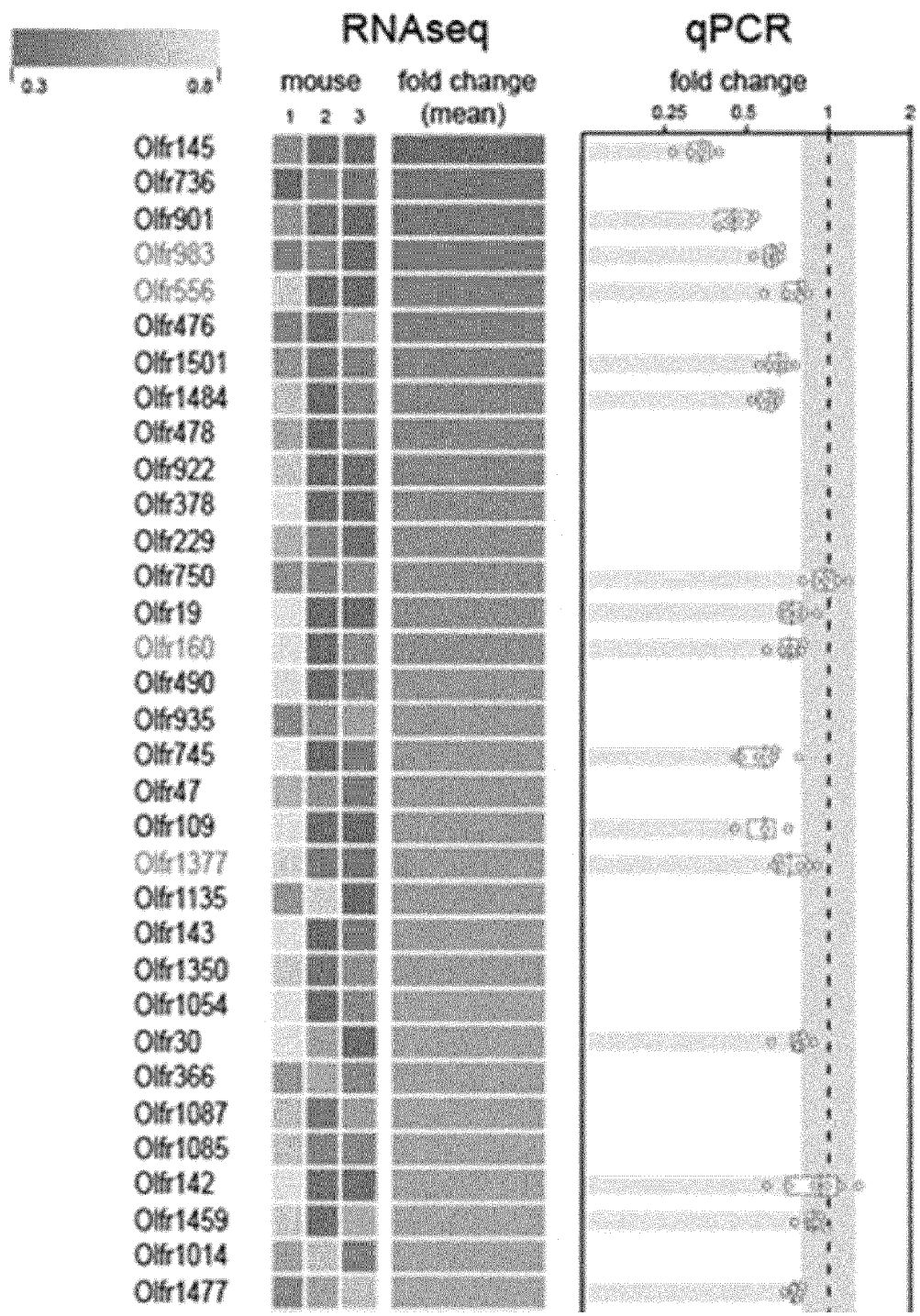
FIG. 3: Transcriptome-wide evaluation of olfactory receptor transcript downregulation after acetophenone exposure. Three mice were exposed per condition, and a library of OR genes was sequenced for each mouse. Black/grey/white rectangles indicate the levels of transcript reduction (from 0.1=90% reduction (black) to 1=0% reduction (white)) relative to the levels present in control mice. Olfr names in grey represent receptor genes whose products were previously shown to be responsive in vitro to acetophenone. Olfr391ps, Olfr1025ps and Olfr1174ps are considered by ENSEMBL as pseudogenes. However, following our own criteria based on sequence signatures, Olfr391ps and Olfr1025ps are considered herewith as potentially functional OR genes and Olfr1174ps as dubious. Right panel: RT-qPCRs of selected OR gene candidates after 5% acetophenone exposure.
Figure 3:
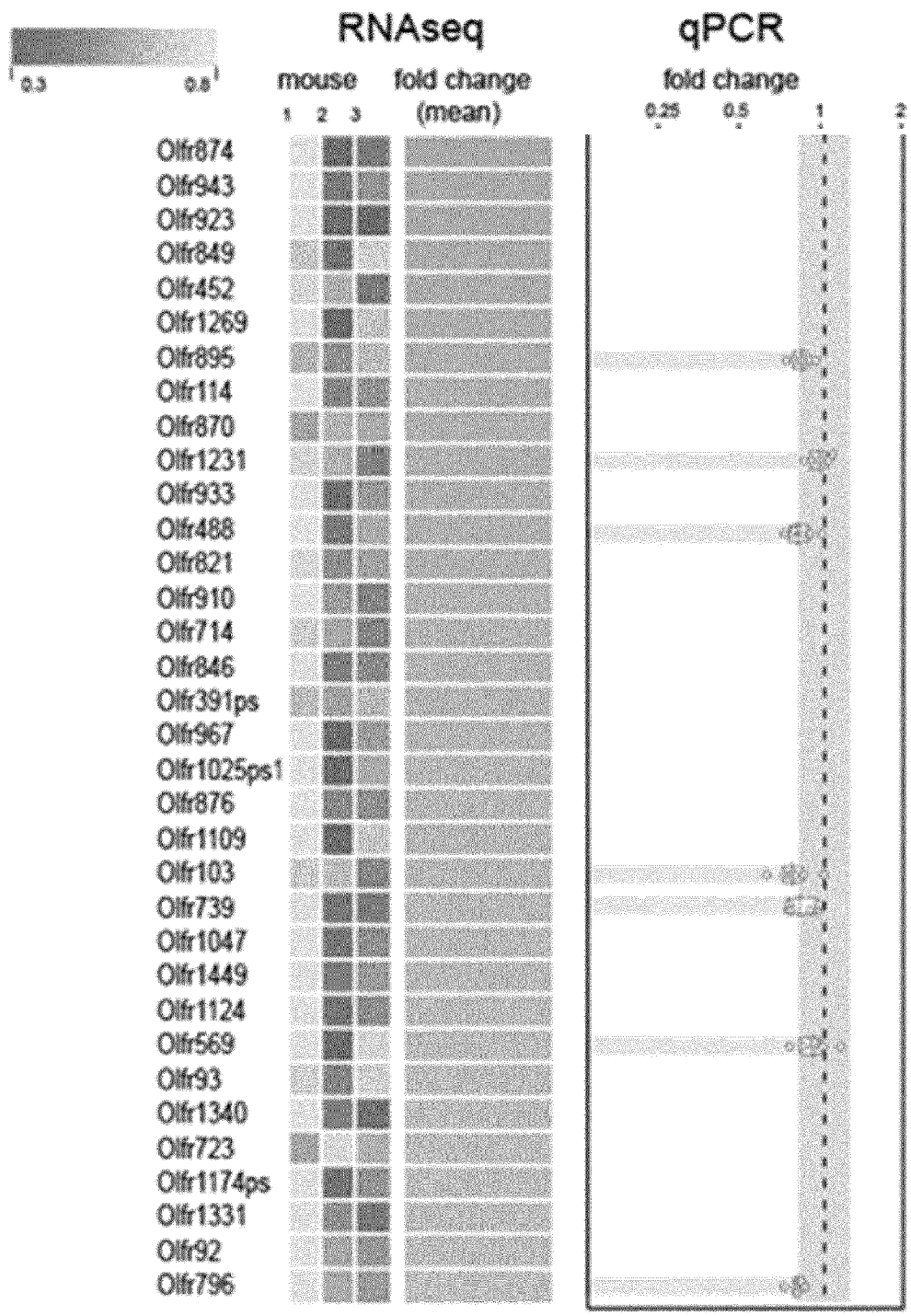

Mice (n=6) were exposed to 5% acetophenone or to a "neutral" control condition for 5 hours. An olfactory cDNA library corresponding to each animal was deep sequenced and the ratios of odorant receptor mRNA concentrations relative to controls were plotted (FIG. 3). Odorant receptor genes that exhibited a transcriptional reduction consistently larger than 20% were considered as downregulated. Based on transcriptional downregulation levels observed by RNAseq following acetophenone exposure, a list of 26 candidate responsive ORs was determined (FIG. 3), that reached 74% decrease (Olfr145) or even over 80% (Olfr169) relative to controls. [Among the identified receptor genes, the four corresponding to the previously known and most sensitive acetophenone receptors (Olfr1377, Olfr556, Olfr983 and Olfr160) were all downregulated, fitting well with the data obtained by RT-qPCR in Example 1 (FIG. 1b). The transcript downregulation of 21 out of the 26 olfactory receptor candidates obtained by RNAseq was confirmed by qPCR. The remaining 5 candidates were false RNAseq positive candidates, namely OR candidates for which in fact mRNA was not downregulated following acetophenone exposure (Table 3).

Figure 4:
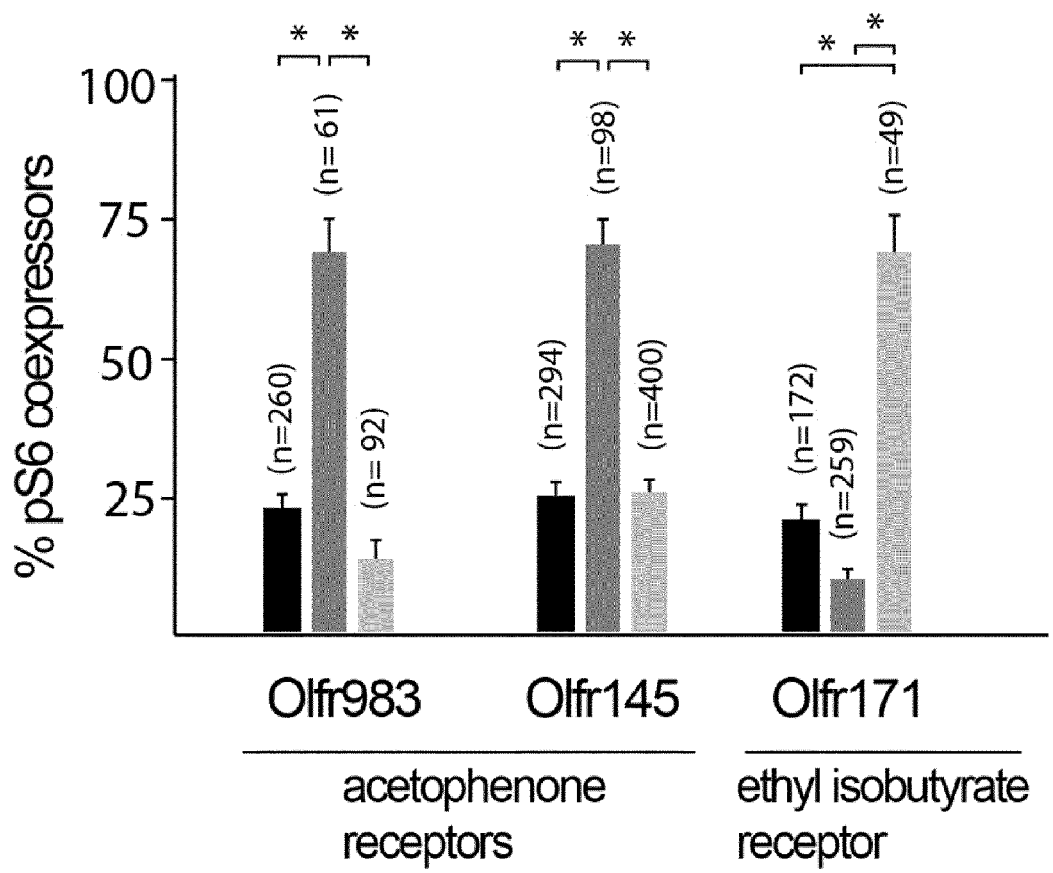
FIG. 4: Neurons whose transcripts are downregulated by odorant exposure are activated neurons. Receptor transcript-specific in situ hybridization followed by immunolabeling of the activity-dependent marker pS6 were performed. Quantification of pS6 coexpression with Olfr983, Olfr171 and Olfr145 after acetophenone or ethyl isobutyrate exposure.

In order to independently validate the identity of an acetophenone receptor obtained with the RNAseq approach, the potential colocalization following acetophenone exposure of a neuronal activity marker (the phosphorylated ribosomal protein S6 (pS6) (Knight et al., 2012, *Cell*, 151, 1126-1137) and specific olfactory receptors were evaluated. To this aim, in-situ hybridizations were performed on sections of olfactory tissue with probes targeting receptor mRNAs followed by immunolabeling of pS6. The probes used were directed against the transcripts of most of the ORs determined as responsive including Olfr983 transcripts (encoding a known acetophenone receptor), Olfr171 transcripts (encoding a known ethyl isobutyrate receptor), and Olfr145 transcripts, encoding a newly identified receptor by RNAseq. Before analysis, mice were exposed to either 5% acetophenone, 5% ethyl isobutyrate, or a negative control condition for 60 minutes. The results indicate that ethyl isobutyrate exposure led to a large fraction of Olfr171-expressing neurons to exhibit signal for pS6 (67%), while neurons expressing Olfr983 and Olfr145 showed pS6 colabeling in only 12% and 28% of the cases respectively (FIG. 4). 66% (Olfr983) and 70% (Olfr145) of the neurons were positive for pS6 after acetophenone exposure, while only 11% of the neurons expressing Olfr171 were positive for pS6 after exposure to this compound. The list of OSN populations (i.e. OSNs expressing the same odorant receptor gene) that exhibited neuronal activation (i.e. pS6 signal in a fraction of neuron exceeding 15% relative to controls) following odorant stimulation is shown in Table 3. A perfect correspondence between olfactory mRNA decrease and pS6 positive signals was observed for all 15 tested OSN populations, and no mRNA modulation and no pS6 signals for all 5 tested OSN populations.

Thus, taken together, the deorphanization approach according to the invention faithfully identifies the neurons that respond as agonists, in vivo, to volatile chemicals.

Therefore, the method according to the invention represents a large scale method for receptor deorphanization following olfactory stimulation.

TABLE 3

|  | candidate ORs (RNAseq) | confirmed by qPCR | ps6 positive |
|---|---|---|---|
| Acetophenone | olfr145 | y | y |
|  | olfr736 | y | na |
|  | olfr901 | y | y |
|  | olfr983 | y | y |
|  | olfr556 | y | y |
|  | olfr476 | y | na |
|  | olfr1501 | y | na |
|  | olfr1448 | y | na |
|  | olfr478 | y | y |
|  | olfr922 | y | y |
|  | olfr229 | y | y |
|  | olfr19 | y | y |
|  | olfr160 | y | y |
|  | olfr935 | y | y |
|  | olfr745 | y | y |
|  | olfr47 | y | na |
|  | olfr109 | y | y |
|  | olfr1377 | y | y |
|  | olfr143 | y | y |
|  | olfr1054 | y | na |
|  | olfr30 | y | y |
|  | olfr378 | n | n |
|  | olfr750 | n | n |
|  | olfr490 | n | n |
|  | olfr1135 | n | n |
|  | olfr1350 | n | n |

Example 4

Production of Transgenic Mice Expressing at Least 10 Human Odorant Receptor Genes Transgenic mice expressing at least 10 human odorant receptor genes are generated.

Human odorant receptor genes (384 genes as cited in paragraph extending from page 26 to 28) can be used. In particular, 209 human odorant receptor genes (cited in full paragraph at page 28) expressed in over 90% of humans with an OR gene repertoire of at least 250 genes are targeted.

To this aim, two separate and independent approaches have been taken: 1) Bacterial Artificial Chromosomes (BACs) of 80-300 kb and containing the human ORs are integrated into the mouse genome following standard procedures.

The nucleic acids are injected into oocyte pronuclei (they can alternatively be delivered to the cells by electroporation, viral delivery, lipofection, or transfection of oocytes or germ cells). The recipient species is not necessarily mice and could be any vertebrate species, in particular rats. The transgene often integrated as it organizes head to tail. These multimeric insertions contain between 1 and a few hundred transgenes that are heterogenous as different transgenes are co-inserted in the genome. The targets to be used can be insertions containing 10-200 transgenes (a situation known to occur in about 1 in 15 founders). All F0 founders are tested for multiple integrations and the identity of the integrants is defined. Complementary founders are crossed to generate a single mouse expressing most human OR genes.

To cover the 209 odorant receptor genes of interest, 94 BACs are co-injected. 2) Conventional transgenes are also generated, each containing an OR promoter followed by a 5'UTR (such as in Vassalli et al., 2002, Neuron, 35(4):681-96), an intron, a human OR coding sequence (one of the 209 OR genes) and a polyA signal. The promoters can be chimeric, and include enhancers/stabilization/choice elements such as in Vassalli et al., 2011, Mol. Cel. Neurosci., 46:381-96. These transgenes are co-injected into mouse oocytes as described above in order to obtain mice expressing most of the human OR genes.

Example 5

Method of the Invention For Identifying Antagonists of Odorant Receptors in Mice Adult C57BL/6 mice were exposed to 5% acetophenone for 5 hours, and the level of transcripts of odorant receptors' genes were measured by RT-qPCR on extracts of olfactory epithelia from these mice, as described in the materials and methods section. The mRNA concentration of Olfr1178 and Olfr730 was significantly increased when exposed to 5% acetophenone (fold changes of 1.5 and 1.4 were observed respectively).

Example 6

Method of the Invention For Deorphanizing Chemoreceptors in *Drosophila*

24 hours-old *Drosphila melanogaster* flies were kept in plastic tubes and exposed to either 5% ethyl lactate diluted in DMSO or to 5% geranyl acetate diluted in DMSO. The odorants were spotted on papers that were introduced into the plastic tubes. 10 flies were used per condition (8 independent extracts per condition). 5 hours after exposure heads were collected and RNA extracted.

Figure 5:
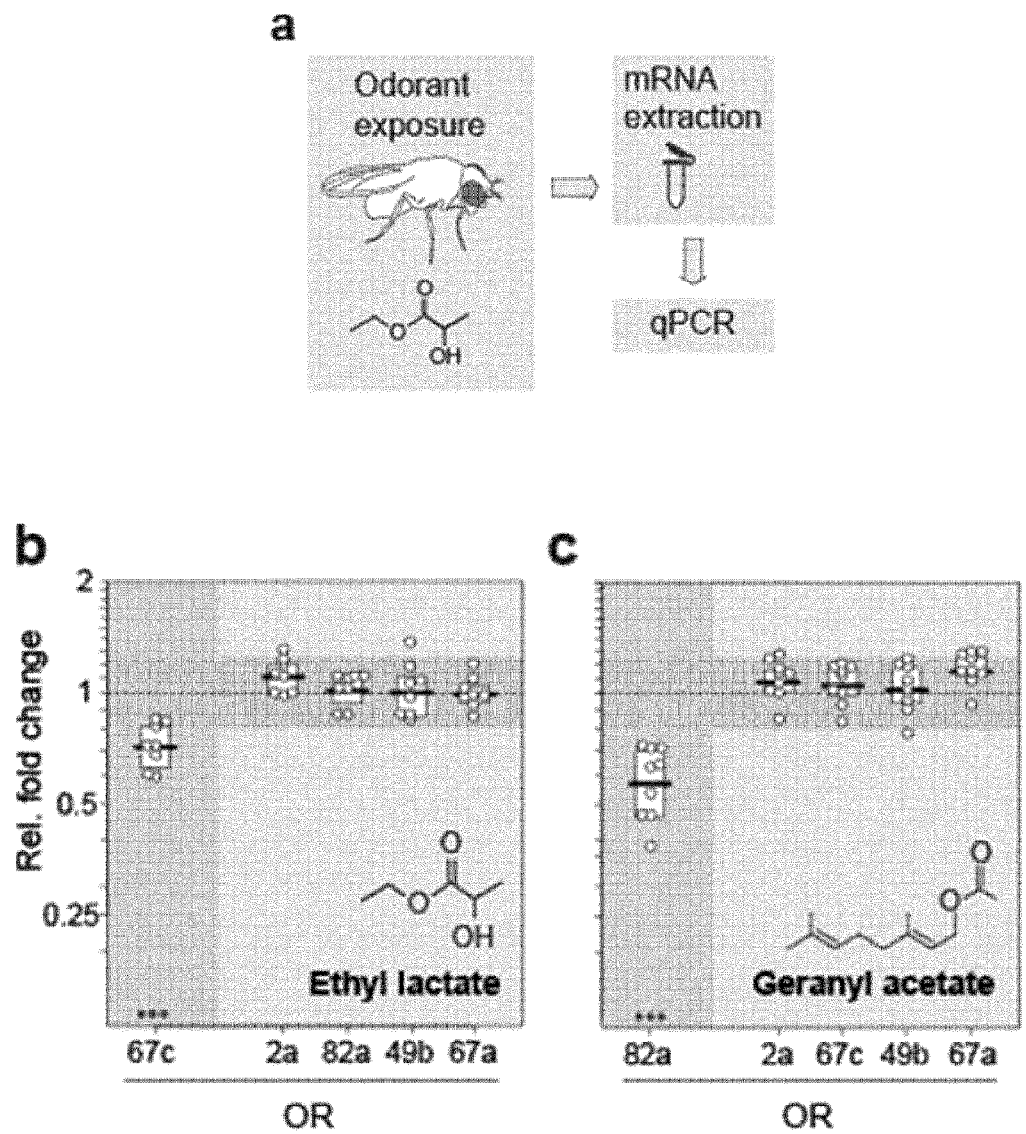
FIG. 5: *Drosophila* OR transcript levels are reduced after agonist stimulation. (a) Schematic representation of the protocol of the method of the invention used as described in Example 6. The amount of OR67c (b) and OR82a (c) mRNA from fly antennae as evaluated by qPCR after 5% ethyl lactate or 5% geranyl acetate exposure for 5 hours. Each dot represents pooled RNA from a vial containing 12 or 25 flies. p values: ***($p<0.001$), two-tailed Mann-Whitney U test between the tested OR gene and all control non-responsive receptor genes.

The transcript levels for Or67c (a known receptor for ethyl lactate) and Or82a (a known receptor for geranyl acetate) were evaluated by RT-qPCR. Or67c mRNA levels were downregulated after ethyl lactate exposure (0.7×) relative to control ORs, and Or82a mRNA levels were downregulated after geranyl acetate exposure (0.6×) relative to control ORs (FIG. 5).

OR67c and OR82a were previously shown to respond to ethyl lactate and geranyl acetate respectively (Hallem and Carlson, 2006, Cell, 125(1):143-60) and of the three negative control olfactory receptors analyzed, Or2a was previously shown to be weakly responsive only to three esters, Or49b was responsive to some aromatic compounds and Or67a was strongly responsive to several odorants (acids, aldehydes, ketones, aromatics, alcohols and esters) (Hallem and Carlson, 2006, supra).

These insect ORs are non-GPCR olfactory receptors, therefore, those data indicate that the present technique applies to a very large variety of chemoreceptors across species, including invertebrates.

SEQUENCE LISTING

| SEQ ID NO. | Forward primer |
|---|---|
| 1 | GAGGGCTAACTAACAGGCCA |
| 3 | ATGCACAGTGGAAGGCTTTG |
| 5 | TGAAGATACCATCTGCCCGC |
| 7 | ACCTGCAGCTCTCACATGAT |
| 9 | CCTGATCATCCTTGGCTCCT |
| 11 | CGCTTCTAAGACTGAACGCC |
| 13 | ATGGCCTTCGATCGGTATGT |
| 15 | AAGGAACCACACTGGGAGAG |
| 17 | CTATCCTTACCCCCATGCTCA |
| 19 | ATTCTAGGGCGGGAAGAAG |
| 21 | CAACCTTCTCTCGAGGCGTA |
| 23 | AGGAGACAGATGCAAAGCCT |
| 25 | TTTTTGTCACCTTGGCCACC |
| 27 | TTGGGATCCTATGCTTGGGG |
| 29 | GAGTGCCTTCTCTTGGCAGT |
| 31 | ACCTGCGGGTCTCATCTTAC |
| 33 | CGCCATGGATTGGAATGAGG |
| 35 | GGTGCCTTCCAAGTACTCCA |
| 37 | CTAAGGCCAACCGTGAAAAGAT |

| SEQ ID NO. | Reverse primer |
|---|---|
| 2 | TCAAGGTGATCATGCCCAGA |
| 4 | CCTAGCCAGGCCACATAGAT |
| 6 | GAAGGACGCATGTAGACACC |
| 8 | ATCCACTGACCCAACAGGAG |
| 10 | CAGAAACCACGGTCAGATGG |
| 12 | CACTTGCCAAATCGGTGGAT |
| 14 | CTCAAGAGGATAGGGGCAGG |
| 16 | CACGTAGGCCAACAGAGAAA |
| 18 | TTCATGGAAGAGAATGTCCCAAG |
| 20 | AGGTGTAAGCAAATGGTGCG |
| 22 | GCCTCCGTACTTCCCAGAAA |
| 24 | CTTGCTGGTCCCTTTTGCAT |
| 26 | ACCAACAAGGCACACATTCC |
| 28 | GACAGATGTGTCAGAGCGTG |
| 30 | GAGCCTGCAGCCAGGAGCCC |
| 32 | TGTAGAACACAGAGGCCCAC |
| 34 | TCGCCAAAGGTGATGAGGAA |
| 36 | AGTGTTCGGGCCAGTTTTTC |
| 38 | CACAGCCTGGATGGCTACGT |

The invention claimed is:

1. A method of identifying at least one olfactory receptor responding to at least one ligand comprising the steps of:
   a) providing a biological sample comprising cells expressing at least one olfactory receptor, wherein said biological sample (i) has been exposed to at least one test compound or (ii) was obtained from an animal that has been exposed to at least one test compound;
   b) measuring the level of mRNAs encoding at least one olfactory receptor in said biological sample, and
   c) comparing the level of mRNAs determined in step b) to the level of mRNAs determined in the same conditions with a negative control where the biological sample or animal has not been exposed to said at least one test compound;
   wherein a difference between the level of mRNAs determined in step b) and the level of mRNAs determined in the same conditions with a negative control indicates that said at least one olfactory receptor responds to said at least one test compound which constitutes a ligand for said at least one olfactory receptor and is able to bind and modulate the activity of said at least one olfactory receptor.

2. The method according to claim 1, wherein said olfactory receptor is a G protein-coupled receptor (GPCR).

3. The method according to claim 1, wherein said olfactory receptor is a trace amine receptor (TAAR).

4. The method according to claim 1, wherein said olfactory receptor is a non-GPCR.

5. The method according to claim 1, wherein said olfactory receptor is a human odorant receptor selected from the group consisting of: OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14A16, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2,OR14I1, OR2C3, OR4A15, OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR8I2, OR10H1, OR1D2, OR2G6, OR4C13, OR51D1, OR5AK2, OR6C3, OR8J1, OR10H2, OR1D5, OR21H1, OR4C15, OR51E1, OR5AN1, OR6C4, OR8J3, OR10H3, OR1E1, OR2H2, OR4C16, OR51E2, OR5AP2, OR6C6, OR8K1, OR10H4, OR1E2, OR2J1, OR4C3, OR51F1, OR5AR1, OR6C65, OR8K3, OR10H5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I1, OR2K2, OR4C6, OR51G2, OR5B12, OR6C74, OR8U1, OR10J5, OR1J1, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, OR5C1, OR6K2, OR9G4, OR10R2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR 1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, OR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11,OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H14, OR2A12, OR2T27, OR4F 6, OR52E2, OR5J2, OR6Y1, OR11H 16, OR2A14, OR2T29, OR4K1, OR52E4, OR5K1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2OR5M11, OR7G1; and/or any variant thereof having an amino acid sequence having at least 80% identity with the amino acid sequence of one of said human olfactory receptors.

6. The method according to claim 1, wherein said biological sample comprises sensory neurons expressing at least one olfactory receptor.

7. The method according to claim 1, wherein said biological sample comprises olfactory sensory neurons expressing at least one olfactory receptor.

8. The method according to claim 1, wherein said biological sample comprises a tissue from the olfactory system.

9. The method according to claim 1, wherein a level of mRNAs determined in step b) in the biological sample after exposure to at least one test compound that is lower than the level of mRNAs determined in the same conditions with a negative control without exposure to a test compound, indicates that said at least one olfactory receptor responds to said at least one test compound which constitutes a ligand acting as an agonist for said at least one olfactory receptor.

10. The method according to claim 1, wherein a level of mRNAs determined in step b) in the biological sample after exposure to at least one test compound that is higher than the level of mRNAs determined in the same conditions with a negative control without exposure to a test compound, indicates that said at least one olfactory receptor responds to said at least one test compound which constitutes a ligand acting as an antagonist for said at least one olfactory receptor.

11. The method according to claim 1, wherein the level of transcription of at least 5 genes, or at least 10 genes encoding an olfactory receptor is determined.

12. The method of claim 1, comprising measuring the level of mRNAs encoding the at least one olfactory receptor in said biological sample immediately after the exposure of the biological sample or the animal to the at least one test compound for about five hours.

* * * * *

SEQUENCE LISTING

<160> NUMBER OF SEQ ID NOS: 38

<210> SEQ ID NO 1
<211> LENGTH: 20
<212> TYPE: DNA
<213> ORGANISM: artificial sequence
<220> FEATURE:
<223> OTHER INFORMATION: Olfr160 fwd primer

<400> SEQUENCE: 1
gagggctaac taacaggcca                    20

<210> SEQ ID NO 2
<211> LENGTH: 20
<212> TYPE: DNA
<213> ORGANISM: artificial sequence
<220> FEATURE:
<223> OTHER INFORMATION: Olfr160 rev primer

<400> SEQUENCE: 2
tcaaggtgat catgcccaga                    20

<210> SEQ ID NO 3
<211> LENGTH: 20
<212> TYPE: DNA

```
<213> ORGANISM: artificial sequence
<220> FEATURE:
<223> OTHER INFORMATION: Olfr556 fwd primer

<400> SEQUENCE: 3
atgcacagtg gaaggctttg                                                    20

<210> SEQ ID NO 4
<211> LENGTH: 20
<212> TYPE: DNA
<213> ORGANISM: artificial sequence
<220> FEATURE:
<223> OTHER INFORMATION: Olfr556 rev primer

<400> SEQUENCE: 4
cctagccagg ccacatagat                                                    20

<210> SEQ ID NO 5
<211> LENGTH: 20
<212> TYPE: DNA
<213> ORGANISM: artificial sequence
<220> FEATURE:
<223> OTHER INFORMATION: Olfr1377 fwd primer

<400> SEQUENCE: 5
tgaagatacc atctgcccgc                                                    20

<210> SEQ ID NO 6
<211> LENGTH: 20
<212> TYPE: DNA
<213> ORGANISM: artificial sequence
<220> FEATURE:
<223> OTHER INFORMATION: Olfr1377 rev primer

<400> SEQUENCE: 6
gaaggacgca tgtagacacc                                                    20

<210> SEQ ID NO 7
<211> LENGTH: 20
<212> TYPE: DNA
<213> ORGANISM: artificial sequence
<220> FEATURE:
<223> OTHER INFORMATION: Olfr983 fwd primer

<400> SEQUENCE: 7
acctgcagct ctcacatgat                                                    20

<210> SEQ ID NO 8
<211> LENGTH: 20
<212> TYPE: DNA
<213> ORGANISM: artificial sequence
<220> FEATURE:
<223> OTHER INFORMATION: Olfr983 rev primer

<400> SEQUENCE: 8
atccactgac ccaacaggag                                                    20

<210> SEQ ID NO 9
<211> LENGTH: 20
<212> TYPE: DNA
<213> ORGANISM: artificial sequence
<220> FEATURE:
<223> OTHER INFORMATION: Olfr1079 fwd primer

<400> SEQUENCE: 9
cctgatcatc cttggctcct                                                    20
```

```
<210> SEQ ID NO 10
<211> LENGTH: 20
<212> TYPE: DNA
<213> ORGANISM: artificial sequence
<220> FEATURE:
<223> OTHER INFORMATION: Olfr1079 rev primer

<400> SEQUENCE: 10
cagaaaccac ggtcagatgg                                               20

<210> SEQ ID NO 11
<211> LENGTH: 20
<212> TYPE: DNA
<213> ORGANISM: artificial sequence
<220> FEATURE:
<223> OTHER INFORMATION: Olfr609 fwd primer

<400> SEQUENCE: 11
cgcttctaag actgaacgcc                                               20

<210> SEQ ID NO 12
<211> LENGTH: 20
<212> TYPE: DNA
<213> ORGANISM: artificial sequence
<220> FEATURE:
<223> OTHER INFORMATION: Olfr609 rev primer

<400> SEQUENCE: 12
cacttgccaa atcggtggat                                               20

<210> SEQ ID NO 13
<211> LENGTH: 20
<212> TYPE: DNA
<213> ORGANISM: artificial sequence
<220> FEATURE:
<223> OTHER INFORMATION: Olfr611 fwd primer

<400> SEQUENCE: 13
atggccttcg atcggtatgt                                               20

<210> SEQ ID NO 14
<211> LENGTH: 20
<212> TYPE: DNA
<213> ORGANISM: artificial sequence
<220> FEATURE:
<223> OTHER INFORMATION: Olfr611 rev primer

<400> SEQUENCE: 14
ctcaagagga tagggcagg                                                20

<210> SEQ ID NO 15
<211> LENGTH: 20
<212> TYPE: DNA
<213> ORGANISM: artificial sequence
<220> FEATURE:
<223> OTHER INFORMATION: Olfr2 fwd primer

<400> SEQUENCE: 15
aaggaaccac actgggagag                                               20

<210> SEQ ID NO 16
<211> LENGTH: 20
<212> TYPE: DNA
<213> ORGANISM: artificial sequence
<220> FEATURE:
```

```
<223> OTHER INFORMATION: Olfr2 rev primer

<400> SEQUENCE: 16
cacgtaggcc aacagagaaa                                                    20

<210> SEQ ID NO 17
<211> LENGTH: 21
<212> TYPE: DNA
<213> ORGANISM: artificial sequence
<220> FEATURE:
<223> OTHER INFORMATION: Olfr168 fwd primer

<400> SEQUENCE: 17
ctatccttac ccccatgctc a                                                  21

<210> SEQ ID NO 18
<211> LENGTH: 23
<212> TYPE: DNA
<213> ORGANISM: artificial sequence
<220> FEATURE:
<223> OTHER INFORMATION: Olfr168 rev primer

<400> SEQUENCE: 18
ttcatggaag agaatgtccc aag                                                23

<210> SEQ ID NO 19
<211> LENGTH: 20
<212> TYPE: DNA
<213> ORGANISM: artificial sequence
<220> FEATURE:
<223> OTHER INFORMATION: Olfr167 fwd primer

<400> SEQUENCE: 19
attctagggc ggggaagaag                                                    20

<210> SEQ ID NO 20
<211> LENGTH: 20
<212> TYPE: DNA
<213> ORGANISM: artificial sequence
<220> FEATURE:
<223> OTHER INFORMATION: Olfr167 rev primer

<400> SEQUENCE: 20
aggtgtaagc aaatggtgcg                                                    20

<210> SEQ ID NO 21
<211> LENGTH: 20
<212> TYPE: DNA
<213> ORGANISM: artificial sequence
<220> FEATURE:
<223> OTHER INFORMATION: Olfr109 fwd primer

<400> SEQUENCE: 21
caaccttctc tcgaggcgta                                                    20

<210> SEQ ID NO 22
<211> LENGTH: 20
<212> TYPE: DNA
<213> ORGANISM: artificial sequence
<220> FEATURE:
<223> OTHER INFORMATION: Olfr109 rev primer

<400> SEQUENCE: 22
gcctccgtac ttcccagaaa                                                    20
```

<210> SEQ ID NO 23
<211> LENGTH: 20
<212> TYPE: DNA
<213> ORGANISM: artificial sequence
<220> FEATURE:
<223> OTHER INFORMATION: Olfr16 fwd primer

<400> SEQUENCE: 23
aggagacaga tgcaaagcct                                              20

<210> SEQ ID NO 24
<211> LENGTH: 20
<212> TYPE: DNA
<213> ORGANISM: artificial sequence
<220> FEATURE:
<223> OTHER INFORMATION: Olfr16 rev primer

<400> SEQUENCE: 24
cttgctggtc ccttttgcat                                              20

<210> SEQ ID NO 25
<211> LENGTH: 20
<212> TYPE: DNA
<213> ORGANISM: artificial sequence
<220> FEATURE:
<223> OTHER INFORMATION: Olfr15 fwd primer

<400> SEQUENCE: 25
tttttgtcac cttggccacc                                              20

<210> SEQ ID NO 26
<211> LENGTH: 20
<212> TYPE: DNA
<213> ORGANISM: artificial sequence
<220> FEATURE:
<223> OTHER INFORMATION: Olfr15 rev primer

<400> SEQUENCE: 26
accaacaagg cacacattcc                                              20

<210> SEQ ID NO 27
<211> LENGTH: 20
<212> TYPE: DNA
<213> ORGANISM: artificial sequence
<220> FEATURE:
<223> OTHER INFORMATION: Olfr73 fwd primer

<400> SEQUENCE: 27
ttgggatcct atgcttgggg                                              20

<210> SEQ ID NO 28
<211> LENGTH: 20
<212> TYPE: DNA
<213> ORGANISM: artificial sequence
<220> FEATURE:
<223> OTHER INFORMATION: Olfr73 rev primer

<400> SEQUENCE: 28
gacagatgtg tcagagcgtg                                              20

<210> SEQ ID NO 29
<211> LENGTH: 20
<212> TYPE: DNA
<213> ORGANISM: artificial sequence
<220> FEATURE:
<223> OTHER INFORMATION: Olfr171 fwd primer

<400> SEQUENCE: 29
gagtgccttc tcttggcagt                                           20

<210> SEQ ID NO 30
<211> LENGTH: 20
<212> TYPE: DNA
<213> ORGANISM: artificial sequence
<220> FEATURE:
<223> OTHER INFORMATION: Olfr171 rev primer

<400> SEQUENCE: 30
gagcctgcag ccaggagccc                                           20

<210> SEQ ID NO 31
<211> LENGTH: 20
<212> TYPE: DNA
<213> ORGANISM: artificial sequence
<220> FEATURE:
<223> OTHER INFORMATION: Olfr1019 fwd primer

<400> SEQUENCE: 31
acctgcgggt ctcatcttac                                           20

<210> SEQ ID NO 32
<211> LENGTH: 20
<212> TYPE: DNA
<213> ORGANISM: artificial sequence
<220> FEATURE:
<223> OTHER INFORMATION: Olfr1019 rev primer

<400> SEQUENCE: 32
tgtagaacac agaggcccac                                           20

<210> SEQ ID NO 33
<211> LENGTH: 20
<212> TYPE: DNA
<213> ORGANISM: artificial sequence
<220> FEATURE:
<223> OTHER INFORMATION: Omp fwd primer

<400> SEQUENCE: 33
cgccatggat tggaatgagg                                           20

<210> SEQ ID NO 34
<211> LENGTH: 20
<212> TYPE: DNA
<213> ORGANISM: artificial sequence
<220> FEATURE:
<223> OTHER INFORMATION: Omp rev primer

<400> SEQUENCE: 34
tcgccaaagg tgatgaggaa                                           20

<210> SEQ ID NO 35
<211> LENGTH: 20
<212> TYPE: DNA
<213> ORGANISM: artificial sequence
<220> FEATURE:
<223> OTHER INFORMATION: Adcy3 fwd primer

<400> SEQUENCE: 35
ggtgccttcc aagtactcca                                           20

<210> SEQ ID NO 36
<211> LENGTH: 20

```
<212> TYPE: DNA
<213> ORGANISM: artificial sequence
<220> FEATURE:
<223> OTHER INFORMATION: Adcy3 rev primer

<400> SEQUENCE: 36
agtgttcggg ccagttttc                                              20

<210> SEQ ID NO 37
<211> LENGTH: 22
<212> TYPE: DNA
<213> ORGANISM: artificial sequence
<220> FEATURE:
<223> OTHER INFORMATION: b Actin fwd primer

<400> SEQUENCE: 37
ctaaggccaa ccgtgaaaag at                                          22

<210> SEQ ID NO 38
<211> LENGTH: 20
<212> TYPE: DNA
<213> ORGANISM: artificial sequence
<220> FEATURE:
<223> OTHER INFORMATION: b Actin rev primer

<400> SEQUENCE: 38
cacagcctgg atggctacgt                                             20
```